(12) United States Patent
Pohl et al.

(10) Patent No.: US 12,134,089 B2
(45) Date of Patent: Nov. 5, 2024

(54) MULTIMODAL CHROMATOGRAPHIC MEDIA FOR PROTEIN SEPARATION

(71) Applicant: DIONEX CORPORATION, Sunnyvale, CA (US)

(72) Inventors: Christopher A. Pohl, Union City, CA (US); Xiaodong Liu, Cupertino, CA (US); Shanhua Lin Liehr, Palo Alto, CA (US)

( * ) Notice: Subject to any disclaimer, the term of this patent is extended or adjusted under 35 U.S.C. 154(b) by 0 days.

(21) Appl. No.: 16/477,752

(22) PCT Filed: Jan. 18, 2018

(86) PCT No.: PCT/US2018/014284
§ 371 (c)(1),
(2) Date: Jul. 12, 2019

(87) PCT Pub. No.: WO2018/136666
PCT Pub. Date: Jul. 26, 2018

(65) Prior Publication Data
US 2019/0358621 A1 Nov. 28, 2019

Related U.S. Application Data

(60) Provisional application No. 62/448,397, filed on Jan. 20, 2017.

(51) Int. Cl.
*B01J 39/20* (2006.01)
*B01D 15/36* (2006.01)
(Continued)

(52) U.S. Cl.
CPC ............ *B01J 39/20* (2013.01); *B01D 15/362* (2013.01); *B01D 15/363* (2013.01);
(Continued)

(58) Field of Classification Search
CPC .. B01J 20/261; B01J 20/28019; B01J 20/288; B01J 20/321; B01J 20/3217;
(Continued)

(56) References Cited

U.S. PATENT DOCUMENTS 4,376,047 A * 3/1983 Pohl ..................... B01D 15/361
  210/198.2
4,606,825 A    8/1986 Crane et al.
(Continued)

FOREIGN PATENT DOCUMENTS

EP    2745903 A1    6/2014
EP    2745904 A1    6/2014
EP    2789387 A1    10/2014

OTHER PUBLICATIONS

Sartorius. "Laboratory Ultrafiltration: Frequently Asked Questions". Sartorius Lab Instruments GmbH & Co. KG. Feb. 2022. (Year: 2022).*

(Continued)

*Primary Examiner* — Ryan B Huang

(57) ABSTRACT

A chromatographic media for separating bio-polymers, the chromatographic media having cationic exchange properties and anionic exchange properties, the chromatographic media comprising: (a) non-porous substrate particles including an organic polymer, the substrate particles having a neutral hydrophilic layer at a surface of the non-porous substrate particles, in which the neutral hydrophilic layer is configured to reduce a binding of the bio-polymers directly to the non-porous substrate particles compared to a binding of the bio-polymer to the non-porous substrate particles without the neutral hydrophilic layer; (b) a charged first ion exchange layer bound to the substrate particles on top of the hydrophilic layer, the first ion exchange layer comprising first ion exchange groups; and (c) a charged second ion (Continued)

exchange layer bound to the substrate particles on top of the first ion exchange layer.

24 Claims, 7 Drawing Sheets

(51) Int. Cl.
| | |
|---|---|
| *B01D 15/38* | (2006.01) |
| *B01J 20/26* | (2006.01) |
| *B01J 20/28* | (2006.01) |
| *B01J 20/288* | (2006.01) |
| *B01J 20/32* | (2006.01) |
| *B01J 39/26* | (2006.01) |
| *B01J 41/14* | (2006.01) |
| *B01J 41/20* | (2006.01) |
| *C07K 1/18* | (2006.01) |

(52) U.S. Cl.
CPC ........ *B01D 15/3847* (2013.01); *B01J 20/261* (2013.01); *B01J 20/28019* (2013.01); *B01J 20/288* (2013.01); *B01J 20/321* (2013.01); *B01J 20/3217* (2013.01); *B01J 20/3278* (2013.01); *B01J 20/3285* (2013.01); *B01J 20/3289* (2013.01); *B01J 20/3293* (2013.01); *B01J 20/3295* (2013.01); *B01J 39/26* (2013.01); *B01J 41/14* (2013.01); *B01J 41/20* (2013.01); *C07K 1/18* (2013.01); *B01J 2220/445* (2013.01)

(58) Field of Classification Search
CPC ................ B01J 20/3278; B01J 20/3285; B01J 20/3289; B01J 20/3293; B01J 20/264; B01J 20/267; B01J 20/3268; B01J 20/328; B01J 20/3295; B01J 39/26; B01J 39/20; B01J 39/18; B01J 39/05; B01J 41/14; B01J 41/20; B01J 41/05; B01J 41/12; B01J 43/00; B01J 2220/445; B01J 39/00; B01J 41/00; B01J 45/00; B01J 47/00; B01J 47/014; B01D 15/362; B01D 15/363; B01D 15/3847; B01D 15/361; B01D 15/364; B01D 15/327; C07K 1/18; G01N 30/02; G01N 30/482; G01N 2030/484; G01N 30/48; G01N 30/96
See application file for complete search history.

(56) References Cited

U.S. PATENT DOCUMENTS

| | | | |
|---|---|---|---|
| 6,914,137 B2* | 7/2005 | Baker | C12N 15/1013 536/25.4 |
| 2005/0242037 A1* | 11/2005 | Berg | B01J 20/286 210/656 |
| 2006/0148104 A1* | 7/2006 | Marini | B82Y 5/00 436/524 |
| 2009/0277838 A1 | 11/2009 | Liu et al. | |
| 2014/0370614 A1* | 12/2014 | Liu | B01J 39/26 422/68.1 |
| 2015/0298097 A1* | 10/2015 | Rahane | B01J 20/3227 210/656 |

OTHER PUBLICATIONS

International Search Report and Written Opinion for Application No. PCT/US2018/014284, mailed Apr. 24, 2018, 15 pages.

* cited by examiner

MULTIMODAL CHROMATOGRAPHIC MEDIA FOR PROTEIN SEPARATION

CROSS-REFERENCE TO RELATED APPLICATION

This application claims priority to U.S. provisional patent application No. 62/448,397, filed on Jan. 20, 2017, entitled "MULTIMODAL CHROMATOGRAPHIC MEDIA FOR PROTEIN SEPARATION," the disclosure of which is incorporated herein by reference

FIELD

This invention relates to the field of chromatographic sample separation that includes liquid chromatography and solid phase extraction. In particular, the invention relates to media for use as a stationary phase in chromatographic sample separation and the synthesis of such media. The invention, in particular, relates to material for use as a multimodal stationary phase. The invention further relates to chromatographic columns containing the stationary phase and applications thereof.

BACKGROUND

Therapeutic proteins are proteins engineered in the laboratory for pharmaceutical use, and have been used to treat cancer, infectious diseases, hemophilia, anemia, multiple sclerosis, hepatitis B/C, amongst other conditions. Therapeutic proteins can permit an individualized treatment approach by supporting a specifically targeted therapeutic process by compensating the deficiency of an essential protein.

Monoclonal antibodies (mAbs) are the most successful and prominent class of therapeutic proteins, currently accounting for approximately one third of total biologics sales and the market is expected to rise further. With their high specificity and excellent biocompatibility, monoclonal antibodies have demonstrated effectiveness against autoimmune disorders, cardiovascular diseases, infectious diseases, and cancer [Seiler F R, Gronski P, Kurrle R, Lüben G, Harthus H P, Ax W, et al. Monoclonal antibodies: their chemistry, functions and possible uses. Angew Chem Int Ed Engl 1985; 24:139-60; Carter P. Improving the efficacy of antibody-based cancer therapies. Nature Rev Cancer 2001; 1:118-29]. The proliferation of monoclonal antibody therapeutics and their susceptibility to various biochemical modifications has increased the emphasis on characterizing these highly heterogeneous products for their safety and efficacy [Cohen S. General structure and heterogeneity of immunoglobulins. Proc R Soc Lond B Biol Sci 1966; 166:114-23; Carson K L. Flexibility—the guiding principle for antibody manufacturing. Nat Biotech 2005; 23:1054-8.].

Liquid chromatography (LC), e.g. HPLC and UHPLC, and solid phase extraction (SPE) are used routinely in analytical chromatography applications. In these chromatographic techniques, separation of a sample comprising a mixture of components (also termed analytes) is achieved by conveying the sample in a liquid mobile phase through a stationary phase in a column, thereby causing the sample to separate into its components due to different partitioning between the mobile and stationary phases of each of the components (i.e. the components have different partition coefficients). The stationary phase is typically in the form of a bed of particles packed within the column, or in the form of a monolithic material held in the column.

The structures of therapeutic proteins (e.g., mAbs) are highly complex and heterogeneous due to various degradation mechanisms including oxidation, reduction, deamidation, isomerization, and lysine truncation. Thus, numerous chromatographic techniques are typically used for characterization of these proteins, including size-exclusion chromatography (SEC), ion exchange chromatography (IEC), and reversed-phase liquid chromatography (RPC).

Proteins such as monoclonal antibody often contain charge variants due to the multiple charged and polar amino acids in its sequence and post translation modifications. Ion-exchange liquid chromatography is the most commonly used chromatography mode for separation of charge variants in therapeutic proteins. This technique utilizes the electrostatic interactions between the proteins and the surface of separation media, and can be divided into either cation exchange (CEX) chromatography or anion-exchange (AEX) chromatography. The choice between these two separation modes depends on the isoelectric point (pI) of the protein of interest and the pH at which the separation is performed. In general, cation exchange chromatography (CEX) is commonly used for basic proteins (protein with pI above 7, such as monoclonal antibody) charge profiling, while anion exchange chromatography (AEX) is considered appropriate for acidic proteins (protein with pI below 7, such as coagulation factor and EPO) charge profiling. In a salt-based method, the pH of mobile phase needs to be optimized for every antibody in order to achieve high resolution separation. Recent advances in the technology have made a dedicated pH gradient buffer system (covering a pH range of 5.6 to 10.2) available to perform the charge-based separation of antibodies on cation-exchange columns [Shanhua Lin, Christopher A. Pohl, Buffer kit and method of generating a linear pH gradient, December 2012, U.S. Pat. No. 8,921,113 B2]. This platform gradient technology is extremely useful in development environments where samples with a broad range of pIs are used and optimizing buffer systems for each sample would typically be a time consuming process. However, the design of pH gradient platform is coupled to stationary phases carrying either positive or negative charges, but not both charges simultaneously. While many therapeutic proteins (e.g., mAbs) can be analyzed by cation-exchange chromatography [Vlasak J, Ionescu R. Heterogeneity of monoclonal antibodies revealed by charge-sensitive methods. Curr Pharm Biotechnol 2008; 9:468-81; DU Y, Walsh A, Ehrick R, Xu W, May K, and Liu H. Chromatographic analysis of the acidic and basic species of recombinant monoclonal antibodies. mAbs 2012; 4: 578-585], a significant portion of protein based drugs (e.g. coagulation factors) require anion-exchange chromatography to be properly retained, separated and characterized [Cheng E1, Jin-zenji D, Lorthiois A P, de Carvalho R R, Tanaka-Azevedo A M, Raw I, Martins E A. Purification of coagulation factor VIII using chromatographic methods. Direct chromatography of plasma in anion exchange resins. Biotechnol Lett. 2010; 9:1207-14]. Conventionally, basic and acidic proteins need to be separated on cation-exchange and anion-exchange chromatography, respectively.

Throughput is a critical factor in bio-pharmaceutical drug development. From an analytical perspective, it is highly desirable to develop a method and appropriate separation media that can retain and separate various proteins with a broad range of pIs within a single injection.

The selectivity of a stationary phase for analytes is mainly governed by column chemistry, which is key in LC separation.

Mixed-mode or multimodal chromatography (MMC) is becoming increasingly popular in pharmaceutical and biopharmaceutical applications due to its unique selectivity and retention of a variety of compounds, especially polar and charged molecules. MMC is a chromatographic method in which solutes interact with stationary phase through more than one interaction mode or mechanism. The use of MMC technology for antibody purification was first developed in the late 1950s with hydroxyapatite [A. Tiselius, S. Hjerten, O. Levin, Protein chromatography on calcium phosphate columns, *Arch. Biochem. Biophys.* 65 (1956) 132-155; S. Hjerten, Calcium phosphate chromatography of normal human serum and of electrophoretically isolated serum proteins, *Biochim. Biophys. Acta* 31 (1959), 216-235]. The following generations of multimode media were developed after 1970 and were used in many applications [B. H. J. Hofstee, R. B. Dunlap (Eds.), Immobilized Biochemicals and Affinity Chromatography, *Plenum Publ. Corp.*, New York, 1974; R. J. Yon, R. J. Simmonds, Protein chromatography on adsorbents with hydrophobic and ionic groups. Purification of human erythrocyte glycophorin, *Biochem. J.* 163 (1977) 397-400; I. Sasaki, H. Gotoh, R. Yamamoto, H. Hasegawa, J. Yamashita, T. Florio, Hydrophobic-Ionic Chromatography: Its Application to Purification of Porcine Pancreas Enzymes, *J. Biochem.* 86 (1979) 1537-1548; W. Kopaciewicz, M. A. Rounds, F. E. Regnier, Stationary phase contributions to retention in high-performance anion-exchange protein chromatography: ligand density and mixed mode effects, *J. Chromatog.* 318 (1985) 157-172. 31]. During the 1980s, these resins were widely used for the purification of nucleic acids rather than the protein purification field. The pioneering work of Burton and Harding started the era of "Hydrophobic Charge Induction Chromatography" or mixed-mode chromatography to purify proteins [S. C. Burton, D. R. K. Harding, Hydrophobic charge induction chromatography: salt independent protein adsorption and facile elution with aqueous buffers, *J. Chromatog.* A 814 (1998) 71-81]. They tested numerous ligands having heterocycles known for their hydrophobicity and demonstrated that the combination of hydrophobic and ionic interactions offered new selectivity. Since then, MMC has been used for mAb purification that does not involve protein A [L. Guerrier, I. Flayeux, E. Boschetti, A dual-mode approach to the selective separation of antibodies and their fragments, *J. Chromatogra. B* 755 (2001) 37-46; M. C. Mowry, M. Meagher, L. Smith, J. Marks, A. Subramanian, Production and purification of a chimeric monoclonal antibody against botulinum neurotoxin serotype A, *Protein Expres. Purif.* 37 (2004) 399-408; S. Ghose, B. Hubbard, S. M. Cramer, Evaluation and comparison of alternatives to Protein A chromatography Mimetic and hydrophobic charge induction chromatographic stationary phases, *J. Chromatogra. A* 1122 (2006) 144-152; H. Bak, O. R. T. Thomas, Evaluation of commercial chromatographic adsorbents for the direct capture of polyclonal rabbit antibodies from clarified antiserum, *J. Chromatogra. B* 848 (2007) 116-130; J. Chen, J. Tetrault, Y. Zhang, A. Wasserman, G. Conley, M. DiLeo, E. Haimes, A. E. Nixon, A. Ley, The distinctive separation attributes of mixed-mode resins and their application in monoclonal antibody downstream purification process, *J. Chromatogra. A* 1217 (2010) 216-224; E. Boschetti, Antibody separation by hydrophobic charge induction chromatography, *Trends Biotechnol.* 20 (2002) 333-337]. MMC using multimodal functional ligands can adsorb target proteins with the combination of ionic interactions, hydrogen bonds and hydrophobic interactions [S. C. Burton, D. R. Harding, Salt-independent adsorption chromatography: new broadspectrum affinity methods for protein capture, *J. Biochem. Biophys. Methods* 49 (2001) 275-287; G. F. Zhao, X. Y. Dong, Y. Sun, Ligands for mixed-mode protein chromatography: Principles, characteristics and design, *J. Biotechnol.* 144 (2009) 3-11; Y. Yang, X. D. Geng, Mixed-mode chromatography and its applications to biopolymers, *J. Chromatogra. A* 1218 (2011) 8813-8825]. Multimode resins can directly capture target proteins at relatively high salt concentration without dilution or other additives due to their multiple binding interactions. Currently, commercially available mixed-mode resins include Capto MMC, Capto adhere and Capto Core 700 from GE Healthcare.

While the above-mentioned multimode separation media have proved to be useful to separate species where misfolding and aggregation has occurred during production of, e.g., recombinant proteins, they don't possess cation-exchange and anion-exchange functionality on the same separation media, thus it is challenging to retain and separate basic and acidic proteins with a single injection using such media.

Liu and co-workers developed Nanopolymer Silica Hybrid (NSH™) technology through electrostatically-driven self-assembly processes. In one embodiment, the separation media consists of high-purity porous spherical silica particles whose inner-pore area is covalently modified with silyl ligands containing both reverse phase (RP) and weak anion exchange (WAX) moieties, while the outer surface is coated with fully sulfonated nano-polymer beads by electrostatic interactions [U.S. Pat. No. 9,314,712]. In another embodiment, the inner-pore area is modified with a covalently bonded hydrophilic layer that also provides cation exchange (CEX) retention while the outer surface is modified with anion exchange (AEX) nano-polymer beads [U.S. Pat. No. 9,310,344]. Such media are available in Trinity™ chromatography columns from Thermo Fisher Scientific Inc. This media is prepared by coating a porous solid support possessing a hydrophilic charged surface with polymer latex particles having the opposite charge via electrostatic attraction (Journal of Chromatography A, 1218 (2011) 3407-3412). Due to the size of the latex particles (>50 nm) being larger than the size of the pores of the porous solid support (<30 nm), the outer surface of the support is functionalized by charged latex particles while the inner-pore area is intact and remains its original functionality and properties. Thus, the size-exclusion effect provides effective spatial separation between the inner-pore area and the outer surface so that the resulting material provides cation-exchange and anion-exchange properties at the same time. In addition, when the porous solid support is modified with both hydrophilic interaction liquid chromatography (HILIC) and ion-exchange (IEX) mixed-mode functionalities, after coating with the charged latex particles, the resulting material provides hydrophilic interaction liquid chromatography (HILIC), cation-exchange and anion-exchange functionalities (X. Liu and C. A. Pohl, *J. Sep. Sci.* 2010, 33, 779-786). The design of this media creates a spatial separation of the AEX and CEX regions, preventing each charged moiety from masking the other, and allowing simultaneous RP (or HILIC), CEX and AEX retention. It has been demonstrated that the columns packed with such media are useful for simultaneous separation of small molecule pharmaceutical drugs and respective counterions and cationic and anionic ions among other applications. However, this media is more limited to small molecules or ions, and is less compatible with larger bio-molecules such as therapeutic proteins mainly due to the undesired interactions associated with surface chemistry and surface morphology.

A further type of separation media available in IonPac CS5 and IonPac CS5A chromatography columns from Thermo Fisher Scientific Inc. comprises hydrophobic polymeric substrates agglomerated with two layers of latex particles (for example, a layer of an anion-exchange latex on top of a layer of a cation-exchange latex). These products are optimized for the separation of transition metals and the cross-link of the latex is too high to be useful for protein chromatography.

SUMMARY

The present invention relates to novel multimodal chromatographic media for protein separations and to methods for making the multimodal separation media. In preferred embodiments, the present invention relates to the preparation of multimodal chromatographic media comprising non-porous polymer particles by providing a hydrophilic surface on the particles. The hydrophilic surface has minimal non-specific binding to biopolymers, such as proteins for example. The preparation further involves creating on the hydrophilic surface both cation-exchange and anion-exchange domains as separate layers. The separation media can exhibit desired selectivity to various proteins with a broad range of pIs.

According to an aspect of the invention there is provided a chromatographic media for separating bio-polymers, the chromatographic media having cationic exchange properties and anionic exchange properties, the chromatographic media comprising:
  non-porous substrate particles composed of organic polymer, the substrate particles having a neutral hydrophilic layer at their surface for minimizing non-specific binding of proteins to the chromatographic media;
  a charged first ion exchange layer bound to the substrate particles on top of the hydrophilic layer, the first ion exchange layer comprising first ion exchange groups;
  a charged second ion exchange layer bound to the substrate particles on top of the first ion exchange layer, the second ion exchange layer comprising second ion exchange groups, the second ion exchange layer having an opposite charge to the first ion exchange layer and being bound to the substrate particles by electrostatic interactions with the first ion exchange layer.

According to another aspect of the invention there is provided a method of preparing a chromatographic media having cationic exchange properties and anionic exchange properties, the chromatographic media comprising the steps:
  providing non-porous substrate particles composed of organic polymer, the substrate particles having a neutral hydrophilic layer at their surface for minimizing non-specific binding of proteins to the chromatographic media;
  attaching a first ion exchange layer comprising first ion exchange groups onto the substrate particles on the neutral hydrophilic layer; and
  attaching a second ion exchange layer onto the substrate particles on top of the first ion exchange layer, the second ion exchange layer comprising second ion exchange groups, the second ion exchange layer having an opposite charge to the first ion exchange layers.

In an embodiment, the non-porous substrate particles may include an organic polymer. In another embodiment, the non-porous substrate particles may consist of an organic polymer. The organic polymer can include or consist of divinylbenzene-based organic polymer such as, for example, a copolymer of divinylbenzene and ethylvinylbenzene, a divinylbenzene polymer, or a styrene-divinylbenzene copolymer. In an embodiment, the non-porous substrate particles include (or consist of) a neutral hydrophilic layer at a surface of the non-porous substrate particles. The neutral hydrophilic layer is configured to reduce a binding of the bio-polymers directly to the non-porous substrate particles compared to a binding of the bio-polymer to the non-porous substrate particles without the neutral hydrophilic layer. The neutral hydrophilic layer may include a fully hydroxylated layer.

The present invention provides multimodal chromatographic media and methods for making multimodal separation media for protein separations. The invention enables the preparation of novel multimodal chromatographic media useful as packing materials for chromatography columns for the effective separation of proteins by creating both cation-exchange and anion-exchange domains on a neutral hydrophilic surface of non-porous substrate particles that has minimal non-specific binding to proteins. The non-specific binding reduces or eliminates problems with carryover and recovery of the protein analytes, which would occur with other media. As a measure of recovery, the neutral hydrophilic layer of the particles can enable at least 50% recovery of α-chymotrypsinogen A as determined by comparing the chromatographic peak area of α-chymotrypsinogen A eluted from a column packed with the substrate particles having the neutral hydrophilic layer (without ion exchange layers present) to the peak area of α-chymotrypsinogen A eluting when a union connection is used in place of the packed column, wherein the latter is designated as 100% recovery. The enabled media exhibit good recovery and the desired selectivity to various proteins with a broad range of pIs. Media of the invention can retain both cationic and anionic molecules within a single analysis. The chromatographic media can simultaneously retain and separate both low pI proteins (e.g., trypsin inhibitor) and high pI proteins (e.g., ribonuclease A) at the same time. Herein, "low pI" proteins refers to acidic proteins (pI<7) and "high pI" proteins refer to basic proteins (pI≥7). The selectivity of the media can be adjusted by changing the chemical composition of the mobile phase. Properties of the mobile phase that can be used to modify the selectivities of the stationary phase include ionic strength, pH and additives, such as organic solvents. The media can be compatible with highly aqueous conditions (e.g., resistant to de-wetting in 100% aqueous conditions) as well as highly organic solvent conditions. The compositions are characterized by a multi-mode retention mechanism, which can include anion-exchange and cation-exchange. The desired primary separation modes are cation-exchange and anion-exchange. However, in some embodiments, a number of secondary interactions may be possible to some extent, e.g. including hydrogen bonding, hydrophobic interaction, pi-pi interaction, etc. Some of these interactions may affect selectivity while some may affect recovery. The compositions are useful not only for making analytical chromatography columns, but also for making solid phase extraction (SPE) columns.

The invention provides a chromatographic media for separating bio-polymers, especially proteins. The chromatographic media are for separating proteins such as mAbs. However, the invention can be useful for separating other bio-polymers, e.g. DNA, RNA, polysaccharides, amongst others. The chromatographic media has cationic exchange properties and anionic exchange properties.

The present invention further provides a composition of the invention in a flow-through bed suitable for use as a chromatographic medium. In addition, the invention provides a chromatography column including a composition of the invention. The invention further provides a chromatography column packed with a separation medium including a composition of the invention.

The present invention further provides a chromatographic method (e.g., for separating analytes in a liquid sample) that involves flowing a liquid through a bed (e.g., packed bed) of a separation medium that includes a composition of the invention. In one example, the liquid (i.e., mobile phase) is an aqueous medium (wherein the majority or all of the medium is water), optionally including an organic solvent.

Also provided are chromatographic devices incorporating the medium of the invention and systems incorporating these devices.

Preferably, the non-porous substrate particles are composed of a divinylbenzene-based organic polymer. Preferably, the non-porous substrate particles are composed of a divinylbenzene polymer or an alkylvinylbenzene-divinylbenzene co-polymer or a styrene-divinylbenzene co-polymer.

Preferably, the median diameter of the substrate particles is in the range 1 to 20 μm. Preferably, the surface area of the substrate particles is in the range 0.5 to 10 $m^2/g$.

Preferably, the neutral hydrophilic layer is a fully hydroxylated layer. Preferably, the hydroxylated layer is provided by surface polymerization, polymer adsorption, cross-linking, or any combination thereof on the surface of the substrate particles. Preferably, the hydroxylated layer is provided by polymerizing a glycidyl monomer, preferably a triglycidyl ether, on the surface of the substrate particles.

Preferably, the first ion exchange layer is polymerized onto the substrate particles. Preferably, the polymerized first ion exchange layer is covalently bound to a neutral hydrophilic layer. Preferably, the polymerized first ion exchange layer is covalently bound to a hydroxide moiety of the neutral hydrophilic layer. Preferably, the first and second ion exchange layers physically contact across the surface of the first ion-exchange layer. Preferably, the first and second ion exchange layers intercalate across the surface of the first ion-exchange layer.

The second ion exchange layer physically can contact an exterior surface of the first ion-exchange layer and the second ion exchange layer may not fully cover all of the first ion-exchange layer. The second ion exchange layer may be a plurality of spheres in which the spheres contact only the exterior of the first ion-exchange layer where the spheres are not buried (or partially intercalated) into the second ion exchange layer where both the first and second ion exchange layers are accessible to bind ions.

In another embodiment, the second ion exchange layer can partially intercalate into the first ion-exchange layer. The second ion exchange layer may be a plurality of spheres or particles (e.g. nanoparticles or latex particles) in which the spheres or particles are partially buried (or partially intercalated) into the first ion exchange layer whereby both the first and second ion exchange layers are accessible to bind ions.

The second ion exchange layer preferably does not interpenetrate too much with the first ion exchange layer, thereby the second ion exchange layer does not quantitatively extinguish the charge (i.e. most of the charge) of the first ion exchange layer. Thus, the presence of the second layer on the first layer preferably does not extinguish the charge (i.e. most of the charge) of the first ion exchange layer. The polymeric structure of the first layer preferably does not allow the second ion exchange layer to interpenetrate too much with the first ion exchange layer, or quantitatively extinguish the charge of the first ion exchange layer. By 'quantitatively extinguish the charge' is also meant that the retention properties (as measured by retention times) of the first ion exchange layer are substantially reduced, e.g. by more than 50%, or by more than 70%, or by more than 90%.

In embodiments of the present invention, both (cationic and anionic) retention modes are provided in a defined geometry on the surface of the non-porous substrate particles, with one retention mode (i.e. in the first layer) directly attached to the substrate and the second retention mode (i.e. in the second layer) directly attached to the first retention mode. In this way, both retention modes reside on the exterior of the non-porous substrate particles. This contrasts with prior art multi-mode media described in EP 2745903 A1 and EP 2745904 A1, in which most of the binding sites for one retention mode reside on the interior surface (i.e. inside the pores) of a porous substrate while the opposite charges and hence binding sites for the other polarity retention mode are applied only to the exterior surface of the substrate particle. The physical separation of the retention modes between the interior and exterior of the porous substrate in the prior art ensures that one retention mode does not extinguish the other. However, the prior art is generally concerned with separations of smaller molecules. The porous property of the prior art substrate is disadvantageous for chromatographic separation of large bio-polymers, such as proteins etc., as it could hinder mass transfer of proteins resulting in low resolution. The ion exchange ligands bound to the substrate in the prior art would be mostly quantitatively extinguished by the attached oppositely charged layer if all binding sites were simply re-located on the exterior of the substrate.

The present invention overcomes the prior art drawbacks in the separation of large bio-polymers, such as proteins etc., by the utilization of non-porous substrate particles. Advantageously, the present invention provides that, on the exterior of the non-porous substrate, both (cationic and anionic) retention modes are provided in a defined geometry on the surface of the substrate wherein one retention mode does not quantitatively extinguish the charge (i.e. most of the charge) of the other retention mode.

Preferably, either (i) the first ion exchange groups are cation exchange groups and are selected from negatively charged sulfonate groups and negatively charged carboxylate groups and the second ion exchange groups are anion exchange groups and are positively charged quaternary amine groups; or (ii) the first ion exchange groups are anion exchange groups and are positively charged quaternary amine groups and the second ion exchange groups are cation exchange groups and are selected from negatively charged sulfonate groups and negatively charged carboxylate groups.

Preferably, the second ion exchange layer comprises charged nano-particles, more preferably latex particles. Preferably, the nano-particles comprise cross-linked latex particles having a median diameter in the range 1-1000 nm. Preferably, the cross-linked latex particles have a degree of crosslinking in the range from 2 to 20%. Preferably, the cross-linked latex particles comprise methacrylate-based polymer.

Preferably, in use, the chromatographic media is disposed in a chromatography column or solid phase extraction column. The column can be used in a method of liquid chromatography comprising separating protein species in a liquid sample by flowing the sample in an eluent through the chromatography column.

Preferably, in the method of preparing a chromatographic media the step of providing the substrate particles having a neutral hydrophilic layer at their surface comprises providing the substrate particles having a fully hydroxylated layer at their surface. Preferably, in the method of preparing a chromatographic media the step of providing the substrate particles having a neutral hydrophilic layer at their surface comprises encapsulating substrate particles with a fully hydroxylated layer through surface polymerization, polymer adsorption, cross-linking, or any combination thereof.

Preferably, in the method of preparing a chromatographic media the step of encapsulating substrate particles with a fully hydroxylated layer comprises polymerization of a triglycidyl ether on the surface of the substrate particles.

Preferably, in the method of preparing a chromatographic media the step of attaching the first ion exchange layer onto the substrate particles comprises one of the steps (i)-(iii):

grafting the first ion exchange layer onto the substrate particles by polymerizing ionic monomers or precursors of ionic monomers, which optionally may comprise co-polymerizing with selected non-ionic monomers;

grafting the first ion exchange layer the first ion exchange layer onto the substrate particles by polymerizing epoxide monomers, which optionally may comprise co-polymerizing with selected other monomers, followed by converting of epoxide groups to anion-exchange or cation-exchange functionality via ring opening reactions; or directly converting surface hydroxyl groups of the hydrophilic layer to anion-exchange or cation-exchange functionality using functional ionic monomer(s), and optionally non-ionic monomer(s).

Preferably, in the method of preparing a chromatographic media, the second layer is attached in step (c) by contacting a slurry of the substrate particles functionalized with the first ion-exchange layer in a liquid medium with a slurry of charged polymer nano-particles. Preferably, in the method of preparing a chromatographic media, the second layer is attached to the substrate particles in step (c) by providing a column packed with the substrate particles functionalized with the first ion-exchange layer as a stationary phase, connecting the column to a pump and pumping a solution or suspension of charged polymer nano-particles through the column such that nano-particles bind to the surface of the substrate particles.

The invention provides a chromatographic media prepared by the described method.

DETAILED DESCRIPTION

Various preferred features, embodiments and examples of the invention will now be described in more detail.

The terms eluent and mobile phase may be used interchangeably and refer to liquid that moves dissolved components (e.g., a glycan) of a mixture that is to be separated through a chromatographic column or other separation device. The mobile phase often contains more than one compound and is a mixture of different solvents or a solution of salts, acids, bases, etc.

The term solvent herein refers to a liquid organic compound (e.g., a single compound) or mixture of compounds. An exemplary solvent is at least partially water miscible. In various embodiments, a solvent is fully water miscible.

Figure 1:
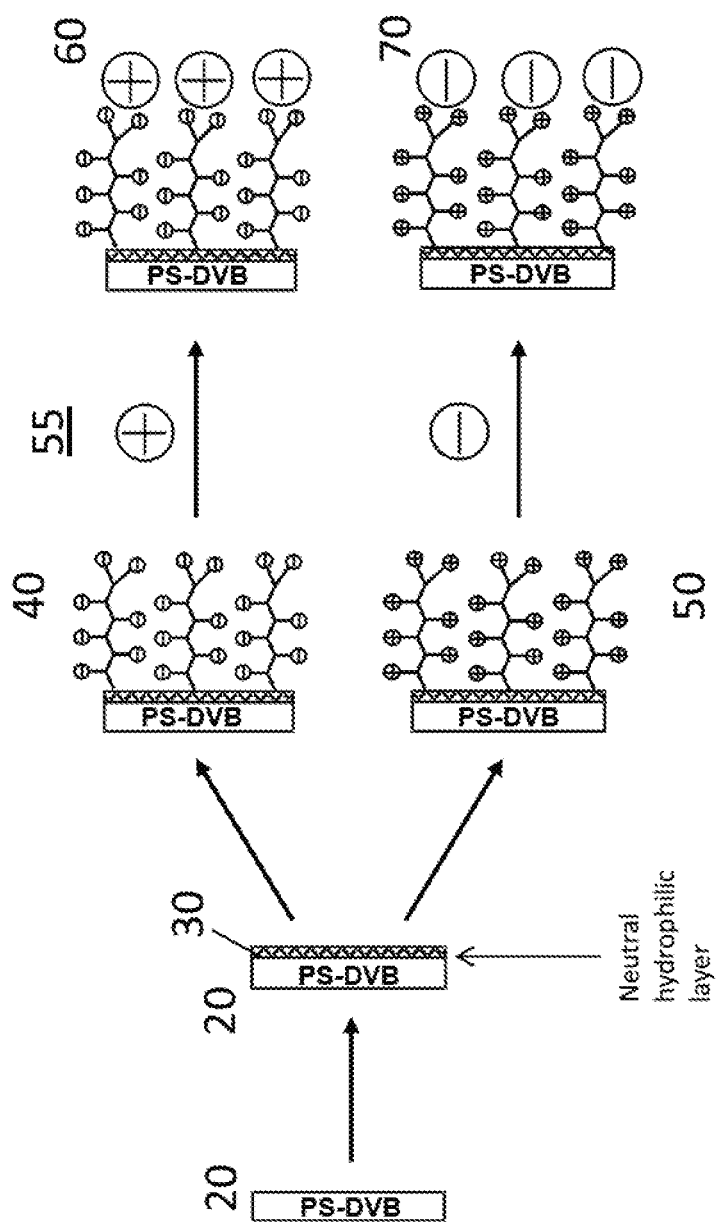
FIG. 1 shows schematically the general structure of multimodal chromatographic media according to the invention, especially useful for protein separations.

FIG. 1 shows schematically on the left hand side of the figure an embodiment of a substrate, which is in the form of non-porous PS-DVB polymer particles of typically median size 10 μm. It is shown as a block which represents a portion of the particle surface 20 of the media but in reality the particles are generally spherical. The substrate particles have a neutral hydrophilic layer 30 on their surface 20. A formation of this layer is described in an example below. The layer 30 is typically fully hydroxylated to minimize non-specific binding of proteins to the chromatographic media. In an embodiment, fully hydroxylated may describe a neutral hydrophilic layer 30 that includes a plurality of hydroxide moieties such that typical protein molecules cannot interact, touch, or bind to particle surface 20. It is worthwhile to note that unmodified particle surface 20 (without layer 30) is hydrophobic and can strongly bind typical protein molecules or bio-polymers, which can cause poor analyte recovery and poor separations in chromatographic applications. In a preferred embodiment, particle surface 20 is fully coated with hydroxide moieties so that there are no bare uncoated spots on particle surface 20 where proteins can strongly bind The presence of hydroxyl groups on particle surface 20 reduces the likelihood of proteins binding to particle surface 20. The hydrophilic layer 30 can then be attached to a charged first ion exchange layer 40 or 50 bound to the substrate particles on top of the hydrophilic layer 30, the first ion exchange layer comprising first ion exchange groups shown schematically as (−) (40) or (+) (50) symbols. Thus, the first ion exchange layer is either a cation exchange layer (40) or an anion exchange layer (50). A charged second ion exchange layer in the form of nano-particles 60, 70 in a step 55 is then bound to the substrate particles on top of the first ion exchange layer 40, 50. The second ion exchange layer nano-particles 60, 70 comprise second ion exchange groups, which have an opposite charge to the first ion exchange layer 40, 50 and are bound to the substrate particles by electrostatic interactions with the first ion exchange layer. Thus, the second ion exchange layer is either a cation exchange layer (70) or an anion exchange layer (60).

The substrate (preferably an organic polymer substrate but which in some embodiments may be silica) is preferably non-porous. In an embodiment, non-porous substrate particles may include pores, which are less than about 10 angstroms. It is worthwhile to note that pore sizes of 10 angstroms or less cannot be easily measured using routine analytical instrumentation. The substrate is particulate. The substrate preferably comprises non-porous particulate media. The non-porosity refers to the individual particles themselves. A packed body of particles within a chromatography column will allow a liquid flow through it due to the spaces or interstices between the non-porous particles. That is, preferably the particles do not have a substantial internal porosity. The substrate of the present invention is desirably a chromatographic media for use, for example, in LC or SPE applications. The substrate is preferably particulate wherein particles of the substrate are typically and preferably substantially spherical but may be irregular in shape in some embodiments. Desirably, the particles of the media are non-porous particles. This has been found to provide better separation of large biopolymers, such as proteins, than porous particles.

The non-porous substrate particles comprise organic polymer (i.e. synthetic resin). The organic polymer particles have been found to provide much improved recovery of large biopolymers, such as proteins, compared with silica-based media of the prior art. The polymer substrate particles of the invention can also better tolerate alkaline conditions that are sometimes used to clean up a chromatography column compared to silica based columns. Polymer based columns are generally more resistant to such conditions (e.g. a PS-DVB substrate can be used at pH 0-14; polymethacrylate at pH 2-12, which compares to silica based substrates at pH 2-8).

The non-porous substrate particles can be composed of polyvinyl resin(s). In particular, the non-porous substrate particles can be composed of poly (vinylaromatic) resin(s), for example those derived from styrene, divinylbenzene, alpha-methylstyrene, chlorostyrene, chloromethylstyrene, vinyltoluene, vinylnaphthalene, or vinylpyridine, or like monomers, or combinations of any two or more thereof (i.e. co-polymers). The non-porous substrate particles can be composed of resins derived from esters of acrylic acid and methacrylic acid, and similar unsaturated monomers. Additional examples include glycidyl acrylate-based and glycidyl methacrylate-based materials (e.g., 2-glycidyloxyethyl methacrylate, vinylbenzyl glycidyl ether, 2-(4-vinylbenzyloxy) ethyl glycidyl ether) as well as those derived from vinylbenzyl chlorides, vinylbenzyl alcohols, 2-(4-vinylbenzyloxy) ethanol, polyacrylamides, polyvinylalcohols, polyvinylformamides. Any of the aforementioned materials can optionally be co-polymerized with monomers incorporating ionic or ionizable functionalities. Any of the above materials used to form the substrate particles preferably can be functionalized to provide a hydroxylated surface on the substrate particles.

In some embodiments, the non-porous substrate particles can comprise cross-linked polymers or co-polymers, for example, PS-DVB copolymer.

Preferably, the non-porous substrate particles comprise a divinylbenzene-based organic polymer, i.e. a polymer derived from at least divinylbenzene monomer, i.e. divinylbenzene monomer alone or divinylbenzene monomer optionally with one or more other monomers (e.g. styrene or preferably an alkylvinylbenzene (especially a C1-C3alkylvinylbenzene), such as ethylvinylbenzene (EVB)). As an example, a commercially available technical grade poly-DVB comprises 55% DVB and 45% ethylvinylbenzene. The divinylbenzene-based polymer preferably comprises at least 50% wt divinylbenzene monomer or at least 60% wt divinylbenzene monomer or at least 70% wt divinylbenzene monomer or at least 80% wt divinylbenzene monomer. In some embodiments, the remainder of can be an alkylvinylbenzene, such as ethylvinylbenzene for example. Preferably, the non-porous substrate particles are composed of a divinylbenzene (DVB) polymer (from divinylbenzene monomer alone or from divinylbenzene monomer and optionally alkylvinylbenzene monomer) or a styrene-divinylbenzene co-polymer (PS-DVB). The substrate particles are preferably without styrene, for example DVB polymer particles without styrene, for improved mechanical strength. However, cross-linked PS-DVB particles, especially highly (>5%) cross-linked PS-DVB, can be used although the mechanical strength may be lower than DVB-only depending on the degree of cross-linking. Alternatively, other organic polymers can be used for the non-porous substrate particles, for example polyvinylalcohol (PVA) particles, or poly(meth)acrylate particles, amongst others.

The particles preferably have a narrow size distribution. In certain examples, the particles are essentially "monodisperse" or essentially "homodisperse", which indicates that the particle size of the majority of the particles (e.g., 80, 90 or 95% of the particles) does not vary substantially (e.g., not more than 10%) below or above the median particle size ($D_{50}$). In an exemplary monodisperse particle population, 90% of the particles have an average particle size of between about $0.9 \times D_{50}$ and about $1.1 \times D_{50}$. This is advantageous for chromatographic applications. Whilst monodispersed particles are preferred, particles with a broader particle size distribution may be useful in many applications.

The substrate particles are typically microparticles, preferably 0.1 μm or larger in median particle diameter, preferably up to 1000 μm in median particle diameter. The particles sizes given herein are measured by a Coulter Counter. More preferably the particles are from 1 to 1000 μm, or 0.1 to 500 μm or 1 to 500 μm in diameter, or still more preferably 0.1 to 100 μm or 1 to 100 μm in diameter, or 0.1 to 50 μm or 1 to 50 μm, or even more preferably 0.1 to 20 μm or 1 to 20 μm in diameter, especially 0.1 to 10 μm or 1 to 10 μm and most preferably 1 to 5 μm in diameter.

In one example, the solid support of the present invention is formed by well-known suspension or emulsion polymerization techniques. In this example, the particles are typically derived from a monomer mixture, which is insoluble in the solvents with which they will be contacted. Exemplary substrates are formed by heating and stirring a suspension of monomers in a suitable solvent in the presence of a suitable emulsifying agent. Alternatively, the polymerization may be carried out by a suspension, bulk or solution process followed by grinding the resin to a desired size by mechanical means (e.g., ball mills, rod mills or the like).

The biopolymers are desirably proteins, e.g. mAbs. However, the invention may be utilized for separating other biopolymers such as DNA, RNA, polysaccharides etc. In preferred embodiments, the MW of the bio-polymer is at least 1000 Da. In some preferred embodiments, the MW of the bio-polymer is at least 5,000, or at least 10,000 Da.

As diffusion kinetics are slow in the case of macromolecules, such as the bio-polymers that the invention is concerned with, diffusion in a porous substrate would tend to increase capacity at the expense of resolving power. The invention enables an improved resolution for proteins by utilizing organic polymer substrate particles that are non-porous.

For the non-porous substrate particles, the (BET) specific surface area of the substrate particles preferably is between about 0.1-30 m²/g, more preferably 0.5-30 m²/g, still more preferably 0.5-20 m²/g and especially 0.5-10 m²/g or 1 to 10 m²/g. For non-porous particles, the median particle diameter is preferably from 1 to 20 μm, or 1 to 10 μm, especially 2 to 10 μm.

The particles of the media have a hydrophilic layer, which is generally neutral (i.e. not electrically charged). The hydrophilic layer has the advantageous property that it provides minimal non-specific binding of proteins, such as mAbs, to the media particles. In this way, the media is made more selective based on the interactions mainly between the proteins or other biopolymers and the two ion exchange layers. Hydrophobic interactions are thereby preferably reduced or eliminated by the hydrophilic layer. The most preferred organic polymers for the substrate particles are substantially hydrophobic, such as DVB or PS-DVB. In that case, the invention utilizes a hydrophilic layer on the surface of the particles to overcome excessive hydrophobic interactions with the underlying substrate. Thus, a purpose of the hydrophilic layer described is to convert a hydrophobic surface of a substrate into a hydrophilic surface prior to attaching the ion exchange layers. Suitable polar groups to provide a highly hydrophilic surface include: hydroxyl (e.g. alcohol groups), ether groups, amide groups, sulfoxide groups and sulfone groups. In preferred embodiments, the neutral hydrophilic layer of the chromatographic media is a fully hydroxylated layer. The non-ionic hydroxyl groups are in contrast to prior art media that utilize a silica substrate. The hydroxyl groups in the present invention are attached to a carbon atom at the surface of the substrate particles. In the case of hydroxyl groups attached to silicon atoms of a silica surface, the hydroxyl causes nonspecific binding effects and poor recovery of proteins, whereas hydroxyl groups attached to carbon in the invention have been found not to cause such problems.

The neutral hydrophilic layer (preferably hydroxyl surface) can mask an otherwise hydrophobic surface or ionic surface thereby minimizing non-desired interaction between the biopolymer molecules, such as proteins, and the media as the stationary phase. In the case of hydrophilic polymer surfaces as such as, for example, polymethacrylate or polyvinylalcohol particles, no additional neutral hydrophilic layer may be needed to be added in the methods of making the media. In other cases, such as preferred DVB-based polymer particles, a neutral hydrophilic layer may need to be formed at the surface of the particles, preferably before the attachment of the first ion exchange layer.

The formation of the neutral hydrophilic surface layer on the substrate may be formed in different ways. In a first option, a hydrophobic polymer substrate (e.g., PS-DVB) is encapsulated with a fully hydroxylated layer through surface polymerization, polymer adsorption, cross-linking, or any combination of these. Thus, preferably, the neutral hydrophilic layer is a polymeric neutral hydrophilic layer. A condensation polymerization is preferred. In a second option, a hydrophilic polymer substrate (e.g., polymethacrylate) has a hydrophilic surface and therefore may not require additional, but may optionally be encapsulated with a fully hydroxylated layer through surface polymerization, polymer adsorption, cross-linking, or a combination of these. Preferably the said processes of surface polymerization, polymer adsorption, cross-linking, or any combination thereof result in a fully hydroxylated surface, i.e. with hydroxyl groups covering the surface of the polymer substrate particles (ideally completely covering the surface of the polymer substrate or to the maximum extent possible), which is most preferable for polymer substrates such as DVB or PS-DVB. Preferably, the hydrophilic layer is coated on the substrate particles, more preferably coated on the substrate particles by polymerization. In a preferred embodiment, organic polymer substrate particles can be encapsulated or coated with a neutral hydrophilic layer. In a more preferred embodiment, divinylbenzene-based polymer substrate particles (e.g. DVB, EVB-DVB or PS-DVB), can be encapsulated or coated with a neutral hydrophilic layer.

The polymer particles can be encapsulated or coated with a neutral hydrophilic layer by polymerizing a glycidyl monomer, such as a glycidyl ether, preferably a diglycidyl ether or triglycidyl ether (for example triglycidyl glycerol ether) on the surface of the substrate particles. A mixture of diglycidyl ether and triglycidyl ether can be used. Other examples of monomers suitable for polymerizing to encapsulate the substrate particles include: triglycidyl glycerol ether, trimethylolpropane triglycidyl ether, or tris(4-hydroxyphenyl)methane triglycidyl ether, or mixtures of any two or more of these with a diglycidyl ether such as glycerol diglycidyl ether. An example of a monomer suitable for polymerization and encapsulation of the polymer particles to provide the neutral hydrophilic layer is given by the Formula I:

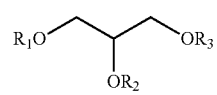

Formula I wherein each of $R_1$, $R_2$, $R_3$ are either H or

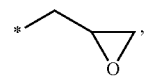

and wherein at least two of $R_1$, $R_2$ and $R_3$ are

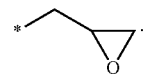

Optionally, in some embodiments, any of the carbon atoms in the formula independently can carry a substituent.

A specific example of a monomer of Formula 1, being a triglycidyl ether, is:

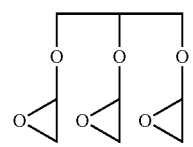 [SMILES: C(OC1CO1)C(COC1CO1)OC1CO1]

The neutral hydrophilic layer is desirably a separate layer to the first ion exchange layer that is present on top of it (and thus also separate to the second ion exchange layer present on top of the first ion exchange layer). The neutral hydrophilic layer thus preferably lies on top of the substrate particles and underneath the first ion exchange layer. The neutral hydrophilic layer, in combination with the ion exchange layers, enables improved protein separation efficiency by assisting to minimize non-specific binding of proteins. In preferred embodiments of the particles of the chromatographic media having the neutral hydrophilic layer thereon at least 50% recovery of α-chymotrypsinogen A can be enabled as determined by comparing the peak area of α-chymotrypsinogen A eluted from a column packed with the media to the peak area of α-chymotrypsinogen A eluting when a union connection is used (in place of the column), wherein the latter is designated as 100% recovery. Thus, for α-chymotrypsinogen A, % recovery=100×(peak area using a packed column)/(peak area using a union in place of the column)

This minimized non-specific binding of proteins provides the desired performance for protein separation that is not obtained with conventional media, which do not provide a neutral hydrophilic layer on the substrate particles.

The multimodal media of the present invention comprise both anion-exchange and cation-exchange domains, desirably as separate layers, i.e. as first and second layers respectively. The multimodal media of the present invention thereby can retain both cationic and anionic biopolymers or biomolecules, preferably with different retention times and for example exhibit unique selectivity for particular biopolymers such as proteins/mAbs with different pIs with both salt and pH gradients. Any combination of strong cation-exchange (SCX), weak cation-exchange (WCX), strong anion exchange (SAX) and weak anion exchange (WAX) can be realized. For example, the cation-exchange layer can be either of strong cation-exchange and weak cation-exchange whilst independently the anion-exchange layer can be either of strong anion exchange or weak anion exchange.

The anion-exchange and cation-exchange domains exist in the media as separate layers on the particles. The order of the layers can be any, i.e. the anion-exchange layer may be the second layer bound on top of the cation-exchange first layer, or alternatively, the anion-exchange layer may be the second layer bound on top of the cation-exchange first layer. The anion-exchange and cation-exchange domains can provide optimal selectivity for biopolymers, such as biologics, with different isoelectric points (pIs). For example, the anion-exchange and cation-exchange domains or layers can be designed by adjusting the ratio of anion-exchange/cation-exchange capacity to yield desired selectivity for specific proteins/mAbs with different pIs.

The first ion exchange groups, in the first ion exchange layer, have a first charge (either positive or negative). The second ion exchange groups, in the second ion exchange layer, have a second charge (either positive or negative), opposite to the first charge. Typically, the layers will be configured so that either: (i) the first ion exchange groups are cation exchange groups and the second ion exchange groups are anion exchange groups; or (ii) the first ion exchange groups are anion exchange groups and the second ion exchange groups are cation exchange groups. Preferably, the layers will be configured so that either (i) the first ion exchange groups are cation exchange groups and are selected from negatively charged sulfonate groups, negatively charged carboxylate groups and negatively charged phosphate groups and the second ion exchange groups are anion exchange groups and are positively charged quaternary amine groups; or (ii) the first ion exchange groups are anion exchange groups and are positively charged quaternary amine groups and the second ion exchange groups are cation exchange groups and are selected from negatively charged sulfonate groups, negatively charged carboxylate groups and negatively charged phosphate groups.

The first ion exchange layer is a functional layer. The first ion exchange layer can be an anion-exchange or cation-exchange layer. The first ion exchange layer is preferably a polymeric layer, for example as hereafter described. The first ion exchange layer preferably comprises polymer chains (i.e. a plurality of polymer chains) bound to the substrate (the substrate having the neutral hydrophilic surface). The polymer chains may be grafted onto the substrate particles by polymerizing appropriate ionic monomers or non-ionic precursors of ionic monomers, which optionally may comprise co-polymerizing with selected non-ionic monomers. The polymer chains have a length, wherein the length preferably extends in a direction orthogonal to the surface of the non-porous substrate particles. Each polymer chain of the first ion exchange layer preferably comprises at least 5, or more preferably at least 10, or more preferably at least 20 ion exchange groups (all of them preferably being the same polarity, either anionic or cationic). The ion exchange groups are preferably distributed along the length of the polymer chain. In some embodiments, each polymer chain of the first ion exchange layer can comprise at least 30, or at least 40 ion exchange groups. Each polymer chain of the first ion exchange layer may comprise up to 100, or up to 80, or up to 70, or up to 60, or up to 50 ion exchange groups. Each polymer chain of the first ion exchange layer may comprise 5 to 100, or 10 to 80, or 20 to 70, or 30 to 60 or 40 to 50 ion exchange groups. In this way, with such a polymeric structure, the first ion exchange layer provides a retention mode on the exterior of the non-porous substrate particles, which cannot be substantially interpenetrated by the second ion exchange layer and/or wherein the second ion exchange layer does not quantitatively extinguish the charge (i.e. most of the charge) of the first ion exchange layer. Thus, the retention properties of the first ion exchange layer are left substantially unaffected by the presence of the second ion exchange layer. In contrast, in the prior art multi-mode media, particular ion exchange ligands are bound to the substrate that would be quantitatively extinguished by the attached oppositely charged layer, since the ion exchange ligands used in the prior art are small molecules, not polymeric, and do not have sufficient length or number of ion exchange groups to be unaffected by the second ion exchange layer. Accordingly, to retain multi-mode properties, the prior art physically separates its first and second retention modes by locating one of the retention modes in the pores of the substrate and locating the other retention mode on the exterior of the substrate. The present invention overcomes the need to physically separate the first and second retention modes in this way and thus advantageously can utilize non-porous substrate particles. Advantageously, the present invention provides that, on the exterior of the non-porous substrate, both (cationic and anionic) retention modes are provided in a defined geometry on the surface of the substrate wherein one retention mode does not quantitatively extinguish the charge of the other retention mode.

As the retention mode of the second ion exchange layer does not quantitatively extinguish the retention mode of the first ion exchange layer, preferably, the retention time of a molecule retained by the first ion exchange layer is not changed by more than 20%, and more preferably is not changed by more than 10%, by the presence of the second ion exchange layer on top of the first ion exchange layer. In other words, retention times of a molecule retained by the first ion exchange layer with and without the second ion exchange layer preferably do not differ by more than 20%, and more preferably do not differ by more 10%.

The first ion exchange layer can be formed directly on the substrate, for example by grafting (i.e. covalent bonding) or electrostatic interactions. The first ion exchange layer can be formed in a number of different ways. According to a first option, the first ion exchange layer is grafted on to the substrate particles (having the hydrophilic layer) by polymerizing appropriate ionic monomers or precursors of ionic monomers, which optionally may comprise co-polymerizing with selected non-ionic monomers. According to a second option, the first ion exchange layer is grafted on to the substrate particles (having the hydrophilic layer) by polymerizing appropriate epoxide monomers, which optionally may comprise co-polymerizing with selected other monomers, followed by conversion of the epoxide groups to anion-exchange or cation-exchange functionality via one or more ring opening reactions. According to a third option, the first ion exchange layer is formed by direct conversion of surface hydroxyl groups of the hydrophilic layer to anion-exchange or cation-exchange functionality using appropriate functional ionic monomer(s), which optionally may comprise co-polymerizing with selected non-ionic monomers.

In some embodiments, the first ion exchange layer is polymerized onto the substrate particles. In some embodiments, the first ion exchange layer can be formed by polymerization in a multi-step process. In a first step, the substrate particles having the hydrophilic layer can be reacted with an ATRP (Atom-transfer radical-polymerization) initiator (e.g. alkyl halide initiator, such as α-bromoisobutyryl bromide (BIBB)), preferably in the presence of an ATRP catalyst (e.g. a copper complex catalyst, such as CuBr) and an ATRP ligand (e.g. a pyridine based ligand), to load the surface of the particles with the initiator. Some specific and non-limiting examples of suitable ATRP initiators include: 2-Azidoethyl 2-bromoisobutyrate, Bis[2-(2'-bromoisobutyryloxy)ethyl]disulfide, Bis[2-(2-bromoisobutyryloxy)undecyl]disulfide, 2-Bromoisobutanoic acid N-hydroxysuccinimide ester, 2-Bromoisobutyric anhydride, α-Bromoisobutyryl bromide, 2-(2-Bromoisobutyryloxy) ethyl methacrylate, tert-Butyl α-bromoisobutyrate, 3-Butynyl 2-bromoisobutyrate, Dipentaerythritol hexakis(2-bromoisobutyrate), Dodecyl 2-bromoisobutyrate, Ethyl α-bromoisobutyrate, Ethylene bis(2-bromoisobutyrate), 2-Hydroxyethyl 2-bromoisobutyrate, 1-(DL-1,2-Isopropylideneglyceryl) 2-bromoisobutyrate, Methyl α-bromoisobutyrate, 2-(4-Morpholino)ethyl 2-bromoisobutyrate contains MEHQ as inhibitor, Octadecyl 2-bromoisobutyrate, Pentaerythritol tetrakis(2-bromoisobutyrate), 1-(Phthalimidomethyl) 2-bromoisobutyrate, Poly(ethylene glycol)bis(2-bromoisobutyrate), Poly(ethylene glycol) methyl ether 2-bromoisobutyrate, Propargyl 2-bromoisobutyrate, 1,1,1-Tris(2-bromoisobutyryloxymethyl)ethane, and 10-Undecenyl 2-bromoisobutyrate. Some specific and non-limiting examples of suitable ATRP ligands include: 1,1,4,7,10,10-Hexamethyltriethylenetetramine, 1,4,8,11-Tetraazacyclotetradecane, 1,4,8,11-Tetramethyl-1,4,8,11-tetraazacyclotetradecane, 2,2'-Bipyridyl ReagentPlus®, 4,4'-Dimethyl-2,2'-dipyridyl, 4,4'-Dinonyl-2,2'-dipyridyl, 4,4'-Di-tert-butyl-2,2'-dipyridyl, N,N,N',N'',N''-Pentamethyldiethylenetriamine, N,N,N',N'-Tetrakis(2-pyridylmethyl)ethylenediamine, N-Butyl-2-pyridylmethanimine, N-Dodecyl-N-(2-pyridylmethylene)amine, N-Octadecyl-N-(2-pyridylmethylene) amine, N-Octyl-2-pyridylmethanimine, Tris(2-pyridylmethyl)amine, and Tris[2-(dimethylamino)ethyl]amine. In a second step, the ATRP initiator loaded particles can be reacted with at least one ionic monomer, optionally with at least one non-ionic monomer, to form the first ion exchange layer by polymerization. The at least one ionic monomer carries at least one cation-exchange group or anion-exchange group. As an alternative second step, the ATRP initiator loaded particles can be reacted with at least one epoxide monomer (e.g. at least one of glycidyloxyethyl methacrylate (GLEMA), glycidyl methacrylate, glycidyldiethylene methacrylate, glycidyltriethylene methacrylate, and glycidylpolyethylene methacrylate), optionally with at least one other monomer, followed by a third step of conversion of the epoxide groups to anion-exchange or cation-exchange functionality via a ring opening reaction. For example, to convert the epoxide groups to quaternary amine anion-exchange groups, an amine, preferably tertiary amine, (e.g. diethanolmethyl amine) can be reacted with the epoxide functionalities. For example, to convert the epoxide groups to sulfonate cation-exchange groups, a sulfonation reaction (e.g. reaction with sodium sulfite ($Na_2SO_3$)) can be employed.

The second ion-exchange layer can be formed on the substrate particles of the media by attaching nano-meter size particles (herein generally termed nano-particles) with opposite charge (to the first charged ion exchange layer) on the outer surface of the first ion-exchange layer, preferably by via electrostatic interactions, or alternatively by covalent bonding, hydrogen bonding, polymer entanglement or other interaction. The nano-particles have a size (median diameter) that is generally from 1 nm to 1000 nm. The nanoparticles can be bound (e.g., irreversibly), either directly or indirectly (e.g., via another layer of nanoparticles), to the exterior surface of the substrate, e.g., via electrostatic forces.

In accordance with the present invention, the second ion-exchange layer is directly on top of the first layer so that they are not substantially physically separated. This contrasts to the prior art in which a substantial physical separation between charged phases is provided, for example by substantially providing for one of the charged domain to reside in the pores of a porous substrate with the other charged domain to reside outside the pores. In preferred embodiments of the present invention, the first and second ion exchange layers physically contact across the surface, and more preferably across substantially the whole surface, i.e. outer surface, of the first ion-exchange layer (e.g. in excess of 80% or 90% of the surface of the first ion-exchange layer). In some preferred embodiments of the present invention, the first and second ion exchange layers can intercalate, preferably over the surface, and more preferably over substantially the whole surface, i.e. outer surface, of the first ion-exchange layer (e.g. in excess of 80% or 90% of the surface of the first ion-exchange layer). Depending upon the relative dimensions of the two layers, in some embodiments one, or both, of the first and second ion exchange layers may have substantially all (e.g. in excess of 70%, 80% or 90%) of its ion-exchange sites paired (i.e. electrically balanced) with opposite charged ion-exchange sites in the other layer. In this way, preferably the media is substantially neutral.

The nanoparticles of use in the present invention can be formed from inorganic or organic material, preferably organic material. The nanoparticles may be formed from any known (e.g., synthetic) ion-exchange resin. Exemplary nanoparticles include a polymeric material, such as a resin polymer (e.g., synthetic resin polymer). Resin polymers are known in the art and include latex and latex-derived materials.

The nano-particles of the present invention can be formed using known techniques and those described herein. In one example, the nano-particles are made using an emulsion polymerization technique. Exemplary nano-particles are formed by heating and stirring a suspension of at least one monomer in a suitable solvent in the presence of a suitable emulsifying agent. Alternatively, the polymerization may be carried out by a suspension, bulk or solution process followed by grinding the resin to a desired size by mechanical means, such as milling (e.g., ball mills, rod mills or the like). In one example, very fine-particles (fines), which form during various polymerization procedures (and are often removed as a side-product), can be used as the nanoparticles in the compositions of the invention.

Charged nano-particles for use as the second ion-exchange layer can be synthesized by a variety of different methods and can be prepared using a wide variety of different monomers. In general, the best chromatography for proteins can be achieved when the polymer matrix is relatively hydrophilic, e.g. when the polymer matrix is a methacrylate-based polymer. For that reason it is preferable to use acrylate or methacrylate based monomers to prepare colloidal nano-particle suspensions. Methacrylate based polymers are preferred because it is more resistant to hydrolytic attack under extreme pH conditions. Generally such particles are synthesized using emulsion polymerization where the continuous phase is water. Under emulsion polymerization conditions the monomer must be insoluble in water in order to prepare nano-particles. In some embodiments, the monomer is a glycidyl acrylate or glycidyl methacrylate (optionally substituted) The preferred functional monomer is glycidyl methacrylate, although other appropriate monomers can be used. Generally the nano-particles will also contain a cross-linker and a diluent monomer. The cross-linker can be any one of a number of readily available dimethacrylate monomers with the most common cross-linking monomers being ethyleneglycoldimethacrylate and diethyleneglycoldimethacrylate. The diluent monomer can be chosen from a wide variety of non-reactive methacrylates. The preferred diluent monomers are methylmethacrylate and hydroxyethylmethacrylate. After synthesis of the nano-particles, the nano-particles are functionalized via a reaction to prepare a variety of ion exchange nanoparticles including strong cation-exchange, weak cation-exchange, strong anion exchange and weak anion exchange.

Alternatively, nano-particles can be formed using reversed emulsion polymerization where the continuous phase is a highly water insoluble solvent. Typically alkanes or perfluoroalkanes are used for continuous phase and reversed emulsion polymerization and monomers are relatively high concentrations solutions dissolved in water. In such systems the preferred monomers are already functionalized with pendant ionizable or ionized groups. Preferably the cross-linking monomer is also ionizable or ionized in order to improve water solubility.

In other examples, nano-particles can be formed from poly(vinylaromatic) resins, such as styrene-divinylbenzene (PS-DVB) copolymer, divinylbenzene-vinylbenzylchloride copolymer, or methacrylate-vinylbenzylchloride copolymer, or divinylbenzene-vinylbenzylglycidylether (or acrylic epoxy type monomers) or other vinyl monomers containing epoxy substituents. Other exemplary nanoparticles include monomers that incorporate reactive functional groups, such as reactive halides (e.g., vinylbenzylbromide or bromoethylmethacrylate) or anhydrides (e.g., co-polymers of maleic anhydride and divinylbenzene).

In one example, the nanoparticle is a latex particle. Latex particles can be derived from latex emulsions.

In a preferred synthesis of cation-exchange nano-particles, strong acid cation exchange latex particles are prepared by synthesizing a cross-linked polystyrene latex using emulsion polymerization and subsequently sulfonating the polystyrene latex upon dilution in sufficient fuming sulfuric acid or chlorosulfonic acid. In another preferred synthesis of cation-exchange nano-particles, weak acid cation-exchange nanoparticles are accomplished by first preparing an emulsion copolymer of a suitable functional monomer and a non-hydrolyzable cross-linking monomer followed by reaction with a tertiary amine. The resulting product is then hydrolyzed in base to produce cross-linked polyacrylic acid (weak cation-exchange) nanoparticles.

In a preferred synthesis of strong anion exchange nano-particles, the particles are synthesized by copolymerizing a suitable functional monomer, cross-linking monomer and diluent monomer. Preferably the functional monomer is glycidylmethacrylate, the cross-linking monomer is ethyleneglycol dimethacrylate and the diluent monomer is hydroxyethy methacrylate. Subsequent to synthesis of the nanoparticles colloidal dispersion the product is reacted with a hydrophilic tertiary amine such as trimethylamine or dimethylethanolamine to produce strong base anion exchange nanoparticles. In another preferred synthesis of anion-exchange nano-particles, weak base anion exchange nanoparticles are accomplished using the same synthetic scheme described above except that the reagent used for functionalization is one of a number of suitable secondary amines. Preferably the reagent is suitably sterically hindered so as to minimize a second cross-linking reaction to form quaternary ion exchange sites. A suitable reagent for this purpose is diethanolamine.

Preferably, the cross-linked latex particles or nano-particles have a degree of crosslinking in the range from 2 to 90%, but more preferably from 2% to 20%, and most preferably from 2 to 10%.

The nanoparticles (e.g., latex-particles) can have any size and shape. In one example, the nanoparticles have a median diameter ranging from about 1 nm to about 1000 nm (1 um). In another example, the nanoparticles have a median diameter ranging from about 1 nm to about 900 nm, from about 1 nm to about 800 nm, from about 1 nm to about 700 nm, from about 1 nm to about 600 nm, from about 1 nm to about 500 nm, from about 1 nm to about 400 nm, from about 1 nm to about 300 nm, from about 1 nm to about 200 nm or from about 1 nm to about 100 nm. In yet another example, the nanoparticles have a median diameter ranging from about 2 nm to about 100 nm, from about 4 nm to about 100 nm, from about 6 nm to about 100 nm, from about 8 nm to about 100 nm, or from about 10 nm to about 100 nm. In yet another example, the nanoparticles have a median diameter ranging from about 10 nm to about 1000 nm, from about 10 nm to about 900 nm, from about 10 nm to about 800 nm, from about 10 nm to about 700 nm, from about 10 nm to about 600 nm, from about 10 nm to about 500 nm, from about 10 nm to about 400 nm, from about 10 nm to about 300 nm, or from about 10 nm to about 200 nm. In one example, the nanoparticle is a latex-particle having an average particle size of between about 2 nm and about 90 nm. In a further example, the nanoparticles have a median diameter of at least about 2 nm, at least about 4 nm, at least about 6 nm, at least about 8 nm, or at least about 10 nm. In another example, the nanoparticles have a median diameter of at least about 20 nm, at least about 30 nm, at least about 40 nm, at least about 50 nm, at least about 60 nm, at least about 70 nm, at least about 80 nm, at least about 90 nm, or at least about 100 nm. In a further example, the nanoparticles have a median diameter of at least about 200 nm, at least about 300 nm, at least about 400 nm, at least about 500 nm, at least about 600 nm, at least about 700 nm, at least about 800 nm, at least about 900 nm; and optionally up to about 1000 nm. In one example the ratio of the average (median) diameter of the substrate particles to the average (median) diameter of the nanoparticles (e.g., latex particles) ranges between about 20:1 to about 5,000:1, or between about 20:1 to about 2,500:1, e.g., from about 20:1 to about 1000:1, or from about 100:1 to about 2500:1.

The second ion-exchange layer is preferably formed by attaching the nano-particles having opposite charge to the first ion-exchange layer on the outer surface of the first ion-exchange layer via electrostatic interactions.

Such attachment of charged nano-particles to the hydrophilic ionic substrate of the opposite charge can be achieved in various ways. In a particular preferred embodiment, the nano-particles can be bound to the substrate by electrostatic force, i.e. interaction. For example, a slurry of the substrate particles functionalized with the first ion-exchange layer in a suitable liquid medium (e.g., aqueous medium) can be contacted with a slurry of charged nano-particles (e.g., functionalized polymer latex particles), i.e. under conditions sufficient for these nano-particles to bind to the surface of the substrate particles. The medium used to prepare the substrate particle slurry and nano-particles slurry is preferably selected so that ion-exchange groups are charged. In one embodiment, the medium is an aqueous medium, which is preferably adjusted to a suitable pH. For example, an anion-exchange surface (e.g., having amino groups) can be suspended in a buffer system (e.g., ammonium acetate) providing a slightly acidic pH (e.g., about pH 5). In another example, a cation-exchange support (e.g., silica functionalized with sulfonated ligands) can be suspended in a buffer system (e.g., ammonium acetate buffer) having a pH that is sufficient to produce de-protonated acidic groups (e.g., about neutral or slightly basic pH). In one embodiment, the nano-particle slurry is used in a sufficient amount to provide an excess of nano-particles. In another example, the two slurries are mixed (e.g., using a mechanical stirrer or shaker) for a sufficient amount of time to obtain a desired degree of nano-particles loading. The reactants are mixed at a suitable temperature. In one example, the temperature is selected between about ambient temperature and about 40° C., preferably about ambient temperature. The resulting mixture can then be filtered and the filter cake may be thoroughly washed and dried to afford a composition of the invention.

Electrostatic attachment of nano-particles to the solid support can alternatively be accomplished through "on-column binding". For example, a column including (e.g. packed with) the ion-exchange substrate as the stationary phase (e.g., the substrate particles functionalized with, i.e. carrying, the first ion-exchange layer) can be connected to a pump (e.g., HPLC pump) and a solution or suspension of nano-particles can be pumped through the column under conditions sufficient for nano-particles to bind to the surface of the substrate. Thus, in preferred embodiments, in a method of making a stationary phase for chromatography column, the second layer is attached to the substrate particles by providing a column packed with the substrate particles functionalized with the first ion-exchange layer as a stationary phase, connecting the column to a pump and pumping a solution or suspension of charged polymer nano-particles through the column such that nano-particles bind to the surface of the substrate particles. During this process, the column is preferably kept at a suitable temperature (e.g., ambient temperature). The nano-particles are preferably pumped through the column for a sufficient amount of time to obtain a desired nano-particle loading of the column. In one example, nano-particles are pumped through the column until nano-particles are exiting the column indicating sufficient loading. For example, by monitoring the column effluent stream for breakthrough of nano-meter size particles, such as latex derived particles, the completion of the nano-particle loading can be determined. The column used in this method can be a packed column.

In preferred embodiments, nano-particles are attached to the exterior surface of the substrate particles, preferably as the outermost layer. The nano-particles preferably are attached to the exterior surface of the substrate particles by any method that precludes removal of the nano-particles from the substrate particles under normal chromatographic conditions, e.g. under the chromatographic conditions used in a method of protein separation by chromatography. For example, nano-particles preferably essentially stay bound to the substrate particles when subjected to strong electrolytes or shearing forces created when a liquid is passed through a bed of the chromatographic material provided by the invention. Such strong or "irreversible" attachment methods include covalent binding, electrostatic attachment (e.g., salt-bridge formation between ionic groups or moieties of opposite charge), polymer entanglement, hydrogen bonding, combinations thereof and any other mechanism providing sufficient force to essentially prevent removal of nano-particles from the substrate during typical chromatographic conditions (e.g., typical LC, flash chromatography, or HPLC, or UHPLC).

Preferably, the BET surface area of the non-porous substrate particles of the chromatographic media is in the range 0.5 to 30 $m^2/g$, or 0.5 to 20 $m^2/g$, or 0.5 to 10 $m^2/g$.

The current invention also provides embodiments, in which the compositions of the invention are contained in a container. The container is preferably a chromatography column. Exemplary chromatography columns include metal columns, glass columns and columns made from a polymeric material, such as plastics. Metal columns may be those commonly used for chromatography procedures employing high pressure (e.g., HPLC, ultra-high pressure, UHPLC). Plastic columns may be those commonly employed for preparative chromatography systems. Such polymeric columns are frequently disposable and are often referred to as cartridges. A metal column may have an inner volume lined with plastic such as polyetheretherketone (PEEK). Hence, in one embodiment, the invention provides a chromatography column packed with a chromatographic media that includes a composition of the invention In yet another example, the invention provides a composition of the invention in a flow-through bed suitable for use as a chromatographic medium.

The current invention further provides a chromatographic method (e.g., for separating analytes, such as proteins, mAbs, and other biopolymers in a liquid sample). The method involves flowing a liquid through a packed bed of chromatographic medium that includes a composition of the invention. In one example, the liquid includes an analyte. For example, the liquid includes at least one type of anion (e.g., organic and/or inorganic anions) and at least one type of cation (e.g., organic and/or inorganic cations) each essentially retained by the chromatographic medium. In another example, the liquid includes at least one type of anion (e.g., organic and/or inorganic anions), at least one type of cation (e.g., organic and/or inorganic cations) and at least one type of uncharged molecule (e.g., hydrophilic molecules, such as glycans), each essentially retained by the chromatographic medium. In yet another example, the above method can be used to separate at least one type of anion (e.g., organic and/or inorganic anions) and at least one type of cation (e.g., organic and/or inorganic cations). In one example, the mobile phase useful in the methods of the invention, includes water. The water content of the mobile phase is preferably between about 0.1% (v/v) and 100% (v/v), more preferably between about 1% and about 100% (v/v), even more preferably between about 10% and about 100% (v/v) and most preferably between about 20% and about 100% (v/v). The invention further provides a method of separating analytes in a liquid sample comprising flowing said liquid sample through a chromatographic medium comprising a composition of the invention. The analytes are preferably proteins or other biopolymers, such as DNA, RNA etc. Preferably the proteins have at least two different pIs. Each of the embodiments and examples outlined herein above for the compositions of the invention, equally apply to the methods of the invention. For example, each embodiment regarding the type of the chromatographic medium, the size of the chromatographic medium, the type and size of the nanoparticles, the type and nature of the ion-exchange groups and the type and nature of the hydrophilic surface as outlined herein above, is equally applicable to the methods of the invention.

The invention can provide a variety of high-performance separation media. The media of the invention may be used in nano-LC, analytical-LC, or SPE. In various embodiments, the media is disposed as a packed bed in a column. For example, a plastic or metal column can be packed with the media.

The material has numerous benefits, such as unique selectivity for a broad range of applications, flexible chemistry such that depending on specific applications the surface chemistry can be tailored accordingly. The chromatographic media can simultaneously retain and separate both low pI proteins (e.g., trypsin inhibitor) and high pI proteins (e.g., ribonuclease A) at the same time. The selectivity of the media can be adjusted by changing the chemical composition of the mobile phase.

Whilst the invention is described herein as being particularly suitable for protein separation, it should be understood that the invention is not so limited and may be used for the separation of other classes of compounds, particularly biopolymers, such as peptides, carbohydrates, polysaccharides, lipids, lipopolysaccharides, nucleic acids, DNA, RNA, aptimers, protein-drug conjugates, and phosphorothioates amongst others.

Specific details of exemplary methods of making the chromatographic media are described in the examples below.

EXAMPLES

In order to enable further understanding of the invention, but without limiting the scope thereof, various exemplary and/or preferred embodiments of the invention are now described with reference to the accompanying drawings.

Figure 2:
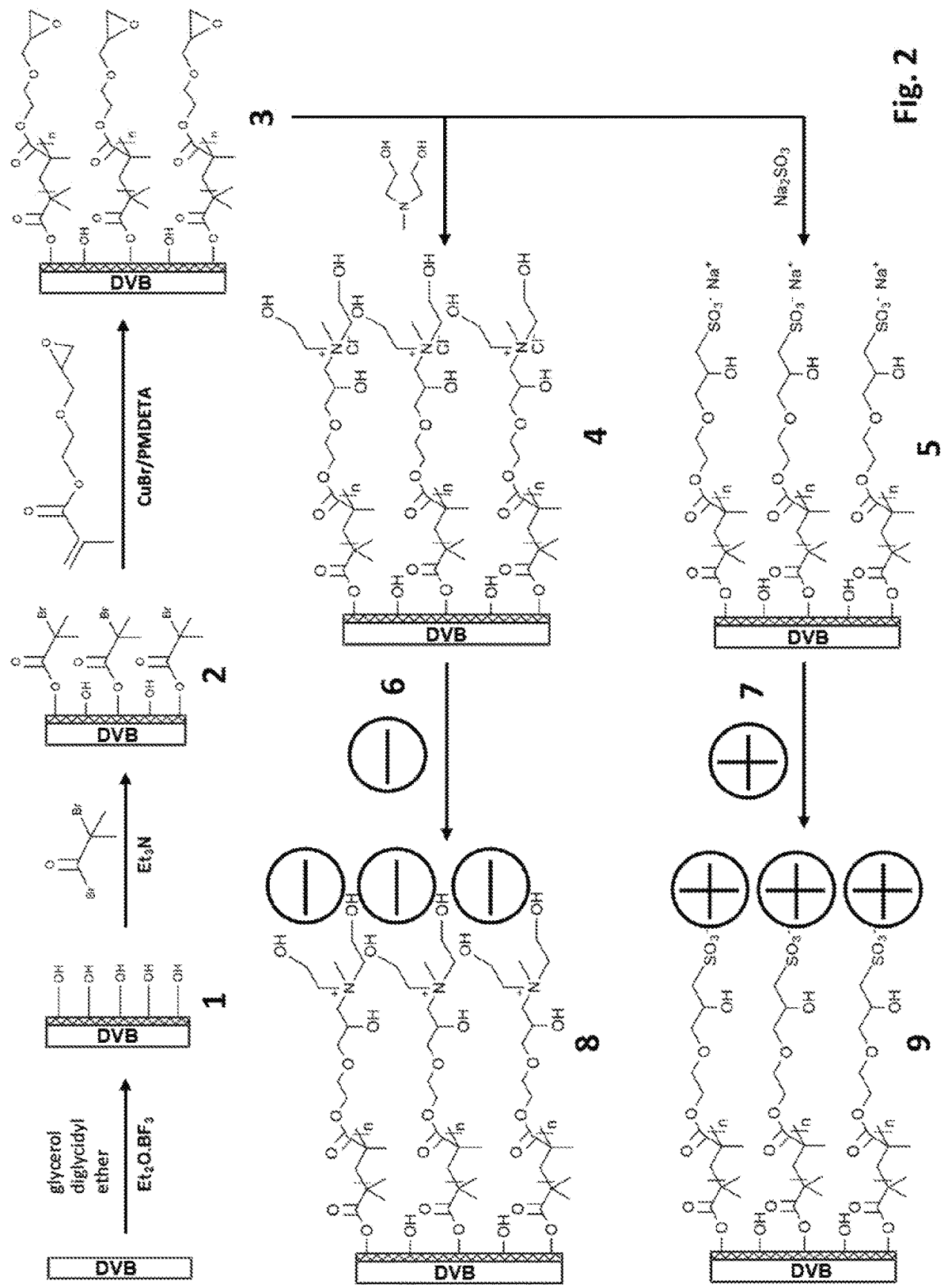
FIG. 2 shows schematically embodiments of synthetic routes for making multimodal chromatographic media according to the invention, in particular synthesis of multimodal media Phases 8 and 9.
Figure 5:
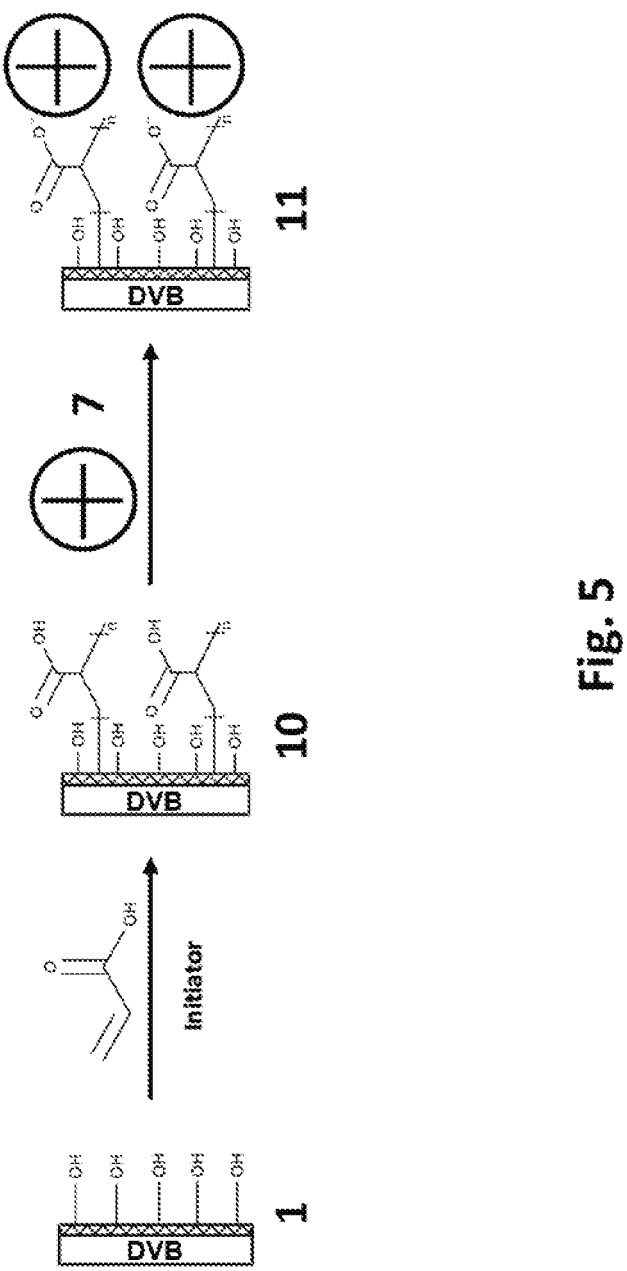
FIG. 5 shows schematically another embodiment of a synthetic route for making multimodal chromatographic media (Phase 11) according to the invention.
Figure 6:
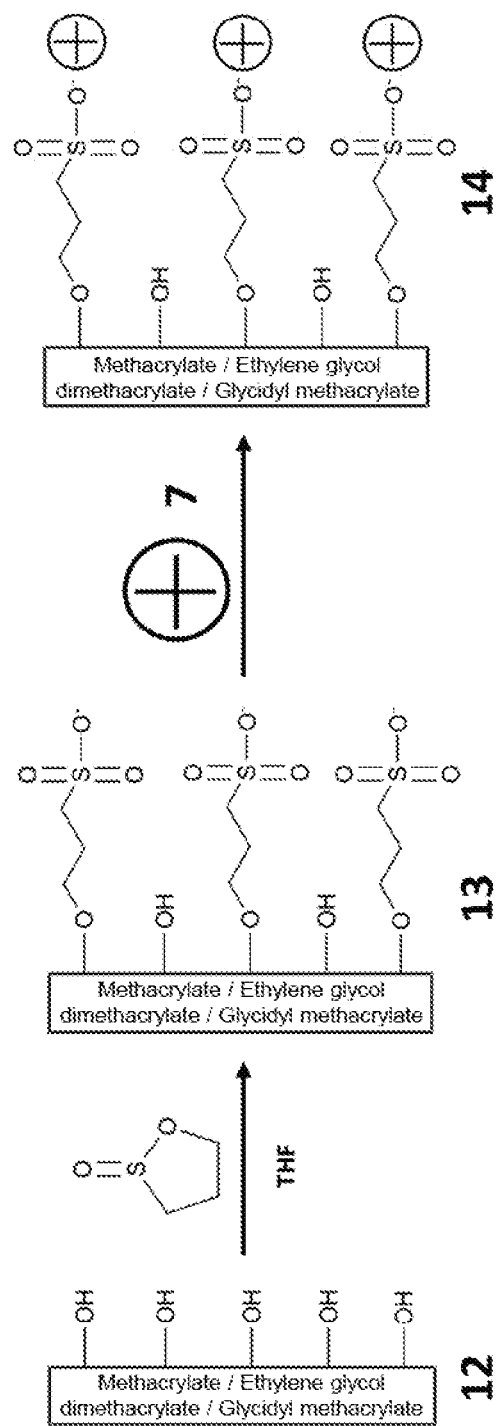
FIG. 6 shows schematically a further embodiment of a synthetic route for making multimodal chromatographic media (Phase 14) according to the invention.

Table 1 summarizes the composition of the phases 8, 9, 11 and 14 shown in FIGS. 2, 5 and 6 that represent chromatographic media of the invention.

TABLE 1

| Phase No. | Substrate | $1^{st}$ ion-exchange layer | $2^{nd}$ ion-exchange layer (nano-particles) |
|---|---|---|---|
| 8 | 10 μm, nonporous, poly-DVB beads with a fully hydroxylated surface (Phase 1) | A pellicular grafted layer having attached quaternary ammonium functional groups (Phase 4) | Sulfonic acid functionalized latex (6) |
| 9 | 10 μm, nonporous, poly-DVB beads coated with a fully hydroxylated surface (Phase 1) | A pellicular grafted layer having attached sulfonate functional groups (Phase 5) | Quaternary amine functionalized latex (raw latex prepared by copolymerization of 2-glycidyloxyethyl methacrylate and di(ethylene glycol) dimethacrylate and then functionalized with methyldiethanol amine) (7) |
| 11 | 10 μm, nonporous, poly-DVB beads with a fully hydroxylated surface (Phase 1) | A pellicular grafted layer having attached carboxylate functional groups (Phase 10) | Quaternary amine functionalized latex (raw latex prepared by copolymerization of 2-glycidyloxyethyl methacrylate and di(ethyleneglycol) dimethacrylate and then functionalized with methyldiethanol amine) (7) |
| 14 | 5 μm, nonporous, poly-methacrylate/glycidyl methacrylate/ethyleneglycoldimethacrylate copolymer with a fully hydroxylated surface (Phase 12) | A pellicular grafted layer having attached sulfonate functional groups (Phase 13) | Quaternary amine functionalized latex (raw latex prepared by copolymerization of 2-glycidyloxyethyl methacrylate and di(ethyleneglycol) dimethacrylate and then functionalized with methyldiethanol amine) (7) |

Example 1

Synthesis of Poly-Divinylbenzene Resin Particles Coated with a Neutral Hydrophilic Layer (1)

Technical grade poly-divinylbenzene (DVB) was used, which is 55% DVB and 45% ethylvinylbenzene (poly-EVB-DVB). However, the particles are referred to throughout these Examples as poly-divinylbenzene (DVB) resin particles for short. To a suspension of 10 g of the technical grade poly-DVB resin (dp=10 μm, spherical, where dp is the diameter of the spherical particle) in 50 mL dioxane (anhydrous) in a 250 mL round bottom flask was added 5 g glycerol triglycidyl ether. After stirring the resulting mixture for 30 min under a nitrogen atmosphere at 50° C., 0.2 mL of boron trifluoride diethyl etherate ($Et_2O \cdot BF_3$) was introduced to start the reaction. After 20 hours at 50° C., the reaction mixture was filtered off and the cake was washed with 200 mL D.I. water, 200 mL 0.5M NaOH (aq.), 400 mL D.I. water, and 200 mL acetone in series. The resulting cake was subjected to 50° C. at reduced pressure to dryness to give Phase 1.

Example 2

Synthesis of ATRP Initiator Loaded Poly-Divinylbenzene Resin Particles (2)

A suspension of 10 g Phase 1 in 50 mL dioxane (anhydrous) in a 250 mL round bottom flask was added to 5 g ($NEt_3$). The resulting mixture was cooled to 5° C. with stirring for 30 min under a nitrogen atmosphere. Then 2 g α-bromoisobutyryl bromide (BIBB) was introduced to the reaction drop-wise. After stirring for 20 hours at ambient temperature, the reaction mixture was filtered off and the cake was washed with 200 mL acetone, 200 mL D.I. water and 200 mL acetone in series. The resulting cake was subjected reduced pressure to dryness to give Phase 2.

Example 3

Synthesis of Polyglycidyl Functionalized Poly-Divinylbenzene Resin Particles (3)

A suspension of 10 g Phase 2 in 50 mL dioxane (anhydrous) in a 250 mL round bottom flask was added to 3 g glycidyloxyethyl methacrylate (GLEMA). After purging the resulting mixture with nitrogen for 15 min, 0.1 g copper (I) bromide (CuBr), 0.12 g N,N,N',N'',N''-Pentamethyldiethylenetriamine (PMDETA) and 0.1 mL ethyl α-bromoisobutyrate were introduced to the reaction in series. After stirring at 40° C. for 5 hours, the reaction mixture was filtered off and the cake was washed with acetone thoroughly 200 mL to give Phase 3, as illustrated in FIG. 2 where n ranges from about 40 to about 50, n being the average number of monomers per polymer chain (i.e. yielding 40 to 50 ion exchange groups per polymer chain of the first ion exchange layer in the resultant phases 4 and 5).

Example 4

Synthesis of Quaternary Amine Functionalized Hydrophilic Coated Poly-Divinylbenzene Resin Particles (4)

A suspension of 5 g Phase 3 in 25 mL dioxane/D.I. water solution (1:1, v/v) in a 100 mL round bottom flask was added to 2 g methyldiethanol amine. After stirring at ambient temperature for 20 hours, the reaction mixture was filtered off and the cake was washed with 100 mL acetone, 100 mL D.I. water, 100 mL acetone to give Phase 4.

Example 5

Synthesis of Sulfonate Functionalized Hydrophilic Coated Poly-Divinylbenzene Resin Particles (5)

A solution of 4 g sodium sulfite ($Na_2SO_3$), 1.2 g sodium phosphate dibasic anhydrous ($Na_2HPO_4$) in 40 g D.I. water in a 100-mL flask was added to 5 g Phase 3. The resulting mixture was purged with nitrogen for 30 min followed by raising the temperature to 52° C. After 20 hours at 52° C., the reaction mixture was filtered off and the cake was washed with 100 mL of 250 mM phosphate buffer at pH 7 and 200 mL D.I. water to give Phase 5.

Example 6

Preparation of Sulfonated Nano-Sized Particles (6)

A de-airated solution of 0.1 g calcium chloride dihydrate in 350 g D.I. water under nitrogen was added to a mixture of 21.66 g styrene, 1.42 g commercial 80.5% divinylbenzene, 0.14 g Vazo 33 (2,2'-azobis (2,4-dimethyl-1-4-methoxyvaleronitrile), 3.66 g Atlox 3403 F (blend of anionic and nonionic surfactants) and 1.09 g Atlox 3404 F. The bottle was capped and tumbled at 32° C. for 17 hours. The mixture was then added to 22 g Igepal DM880 (ethoxylated dialkylphenol). The bottle was again capped and tumbled for 24 hours at 32° C. The reaction mixture was filtered using Whatman's GF/A, GF/D and GF/F filters to remove any coagulum from the latex.

The latex was sulfonated by adding 92.4 g concentrated sulfuric acid to 20 g of the filtered latex. To the mixture were added 137 g chlorosulfonic acid. The mixture was heated at 110° C. for 2 hours and was then cooled to 60° C. The cooled mixture was added to 3.22M sodium hydroxide (1800 ml) to quench the sulfonation of the latex. The quenched latex was filtered using a Whatman #541 filter to remove coagulum to give sulfonated 4-methylstyrene/divinylstyrene latex 6 (5% crosslinking, dp: 150 nm).

Example 7

Preparation of Quaternary Aminated Polymethacrylate Nano-Meter Sized Particles (7)

A mixture of 24 g of 2-glycidyloxyethyl methacrylate and 8 g of di(ethylene glycol) dimethacrylate (DEGDMA) was added to 320 g of an aqueous solution containing 8 g of 70% Triton X-405 (a nonionic ethoxylated alkylphenol), 0.5 g of potassium persulfate, and 0.5 g of potassium metabisulfite. The mixture was de-airated with nitrogen for 20 minutes. The bottle was capped and tumbled in a water bath held at 32° C. for 18 hours. The resulting latex was then added to 19.2 g of a 70% Triton X-405 solution. The white opaque mixture was filtered through a GF/A glass fiber filter paper to remove any coagulum and to afford a latex solution.

The latex was added to a mixture of 62.4 g of 1M nitric acid and 91.2 g of 5M methyldiethanol amine to form aminated, quaternized latex. The mixture was stirred for 10 minutes. An additional mixture of 144 g 1M nitric acid and 384 g 5M methyldiethanol amine was added and stirring was continued for 12 hours at 50° C. to give the aminated latex 7 (~5% crosslinking, dp: 80 nm).

Example 8

Preparation of SAX(SCX) Multimode Media (8)

5 g the positively charged material (Phase 4 of Example 4) was dispersed in 100 mL of ammonium acetate buffer (100 mM, pH 5). Separately, 100 mL of sulfonated latex 6

(Example 6) were adjusted to pH 4-5 with an ammonium acetate buffer (2 M, pH 5.4). The Phase 4 dispersion and the sulfonated latex mixture were combined and the resulting mixture was stirred at ambient temperature for 3 hours. The cake was filtered off and thoroughly washed with 0.1% acetic acid solution (aq.) followed by acetone to give the Phase 8.

Example 9

Preparation of SCX(SAX) Multi-Mode Media (9)

A 4.0×50 mm PEEK LC column was packed with material 5 (of Example 5) using a high-pressure slurry packing technique. Separately, 10 mL of an aminated latex solution 7 (of Example 7) was adjusted to pH 7-8 with a phosphate buffer (0.2 M, pH7 to 8). The latex solution was transferred into a 250-mL HPLC eluent bottle. A HPLC pump was used to wash the packed column with a phosphate buffer (0.2 M, pH 7) at 0.5 mL/min for 30 min. The column was then purged with the latex solution at 0.5 mL/min until the latex particles were observed flowing out the exit of the column. Finally, the column was washed with phosphate buffer (0.2 M, pH7), D.I water, and 70% acetonitrile in D.I. water to afford a column packed with Phase 9.

Example 10

Characterization of Bio-Compatibility of Polymer Resin Particles Coated with a Neutral Hydrophilic Layer A test was designed to measure the desired bio-compatibility provided by the neutral hydrophilic layer (Phase 1) before any ion exchange functionality was applied to the particles. The bio-compatibility was assessed in terms of the degree of protein recovery from the column, the higher the recovery the better. For the characterization, 4.0×50 mm PEEK LC columns were packed with the material of Phase 1, which was coated with a neutral hydrophilic hydroxyl layer. Isocratic test conditions were used: mobile phase, 100 mM sodium phosphate buffer at pH 7.0; flow rate, 0.2 mL/min; injection volume, 2 µL; temperature, 30° C.; detection, UV at 280 nm. A test protein was used: α-chymotrypsinogen A (1 mg/mL). The peak areas of α-chymotrypsinogen A were recorded for each chromatographic run using the test conditions. For a control experiment, a union (e.g., an empty cylindrical housing) was used instead of a column packed with Phase 1 and the resulting peak area was designated as 100% recovery. The bio-compatibility of a resin coated with a neutral hydrophilic surface in accordance with the invention was determined by the recovery of α-chymotrypsinogen A from the column, which was derived by comparing the peak area obtained on the specific media to that obtained from the union configuration. For comparison purpose, a raw PS-DVB resin without a neutral hydrophilic layer was tested with 2.45% recovery indicating that α-chymotrypsinogen A bound strongly to the hydrophobic surface of the PS-DVB resin. It was determined that a minimum of 50% recovery of α-chymotrypsinogen A was required to ensure the desired performance for protein separation. Greater than 70% recovery was generally observed with the materials of the invention (Phase 1).

Example 11

Simultaneous Separation of Low pI and High pI Protein(s) on the Multimode Phase Containing Anion-Exchange Layer on Nonporous Particles with Cation-Exchange Nano-Particles (Phase 8) and without Cation-Exchange Nano-Particles (Phase 4)

Two 4.0×50 mm PEEK LC columns packed with Phase 8 and Phase 4 respectively and were subjected to the following chromatographic evaluation. The test conditions were as follows: gradient, 20 mM Tris (2-Amino-2-(hydroxymethyl)-1,3-propanediol) and 0 mM NaCl to 20 mM Tris and 500 mM NaCl at pH 8.5 over 10 min (where the NaCl concentration increased linearly); flow rate, 1 mL/min; injection volume, 5 µL; temperature: 30° C.; detection, UV at 280 nm. The test mixture contained trypsin inhibitor (5 mg/mL) and ribonuclease A (5 mg/mL).

Figure 3:
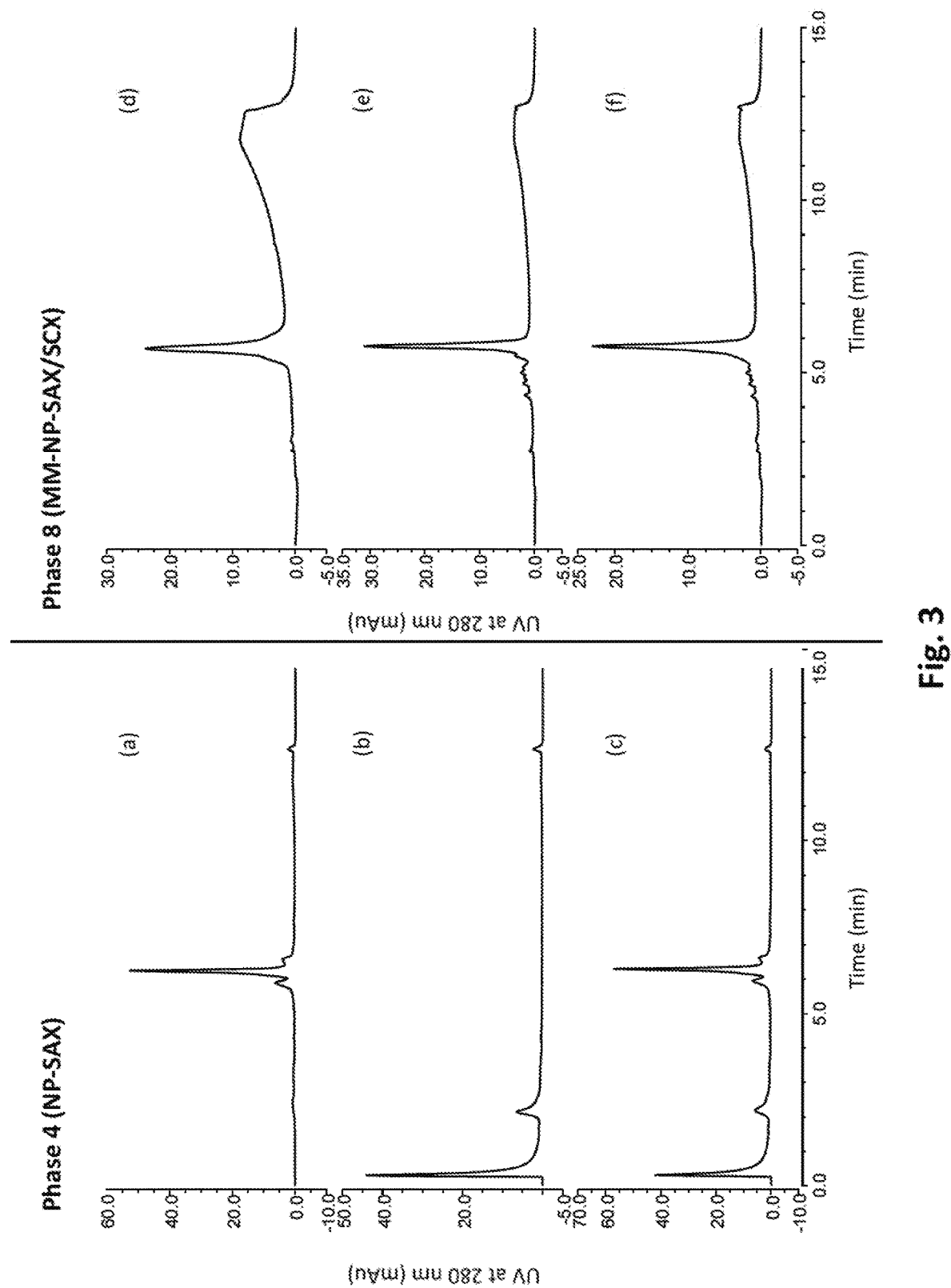
FIG. 3 shows various chromatograms illustrating the simultaneous retention and separation of both low pI and high pI proteins using a chromatographic media (Phase 8 shown in FIG. 2) according to the invention (chromatograms d-f) and using a comparative chromatographic media (Phase 4, chromatograms a-c).

FIG. 3 demonstrates the simultaneous separation of these low pI and high pI proteins on the multimode phase (Phase 8) containing an anion-exchange layer (on non-porous particles) with cation-exchange nano-size particles. FIG. 3 (chromatograms a, b and c) show that at pH 8.5, Phase 4 (anion-exchange media, without opposite charged nano particles) retains low pI proteins such as trypsin inhibitor (RT at 5.04 min) (run of trypsin inhibitor only, chromatogram 3a) and its charge variants through electrostatic attractions but excludes high pI proteins such as ribonuclease A (run of ribonuclease A only, chromatogram 3b) due to electrostatic repulsion. Chromatogram 3c shows a run on a sample of both trypsin inhibitor and ribonuclease A. It is worthwhile to note that ribonuclease A eluted from the column in the void volume because it was not retained by Phase 4. For this reason, Phase 4 is not predicted to be effective for separating charge variants of ribonuclease A under the chromatographic conditions of this Example because ribonuclease A and its charge variants would all elute in the void volume.

By comparison, combining anion-exchange (from Phase 4) and cation-exchange (from latex 6) characteristics, Phase 8 can simultaneously retain both low pI proteins (e.g., trypsin inhibitor) and high pI proteins (e.g., ribonuclease A) at the same time (FIG. 3, chromatograms d, e and f, where d was run with trypsin inhibitor, e was run with ribonuclease A and f was run on a sample of both trypsin inhibitor and ribonuclease A, which show that both proteins were retained and co-elute). Although the peaks in FIG. 3f are coincident, Applicant believes that since Phase 8 retains and elutes both trypsin inhibitor and ribonuclease A, optimization of the chromatographic conditions such as adjusting the salt gradient, pH, or change in buffer salt will result in a better separation of trypsin inhibitor and ribonuclease A using Phase 8. This optimized separation will allow analysis of charge variants of the trypsin inhibitor and ribonuclease A in a single chromatographic run.

Example 12

Simultaneous Separation of High pI and Low pI Protein(s) on the Multimode Phase Containing Cation-Exchange Layer on Nonporous Particles with Anion-Exchange Nano-Size Particles (Phase 9) and without Anion-Exchange Nano-Particles (Phase 5)

Two 4.0×50 mm PEEK LC columns packed with Phase 9 and Phase 5, respectively were subjected to the following chromatographic evaluation. The test conditions were as follows: gradient, 20 mM MES (2-(N-Morpholino)ethanesulfonic acid) and 0 mM NaCl to 20 mM MES and 500 mM NaCl at pH 5.6 over 10 min (where the NaCl concentration increased linearly); flow rate, 1 mL/min; injection volume, 5 µL; temperature: 30° C.; detection, UV at 280 nm. The test mixture contained trypsin inhibitor (5 mg/mL) and ribonuclease A (5 mg/mL).

Figure 4:
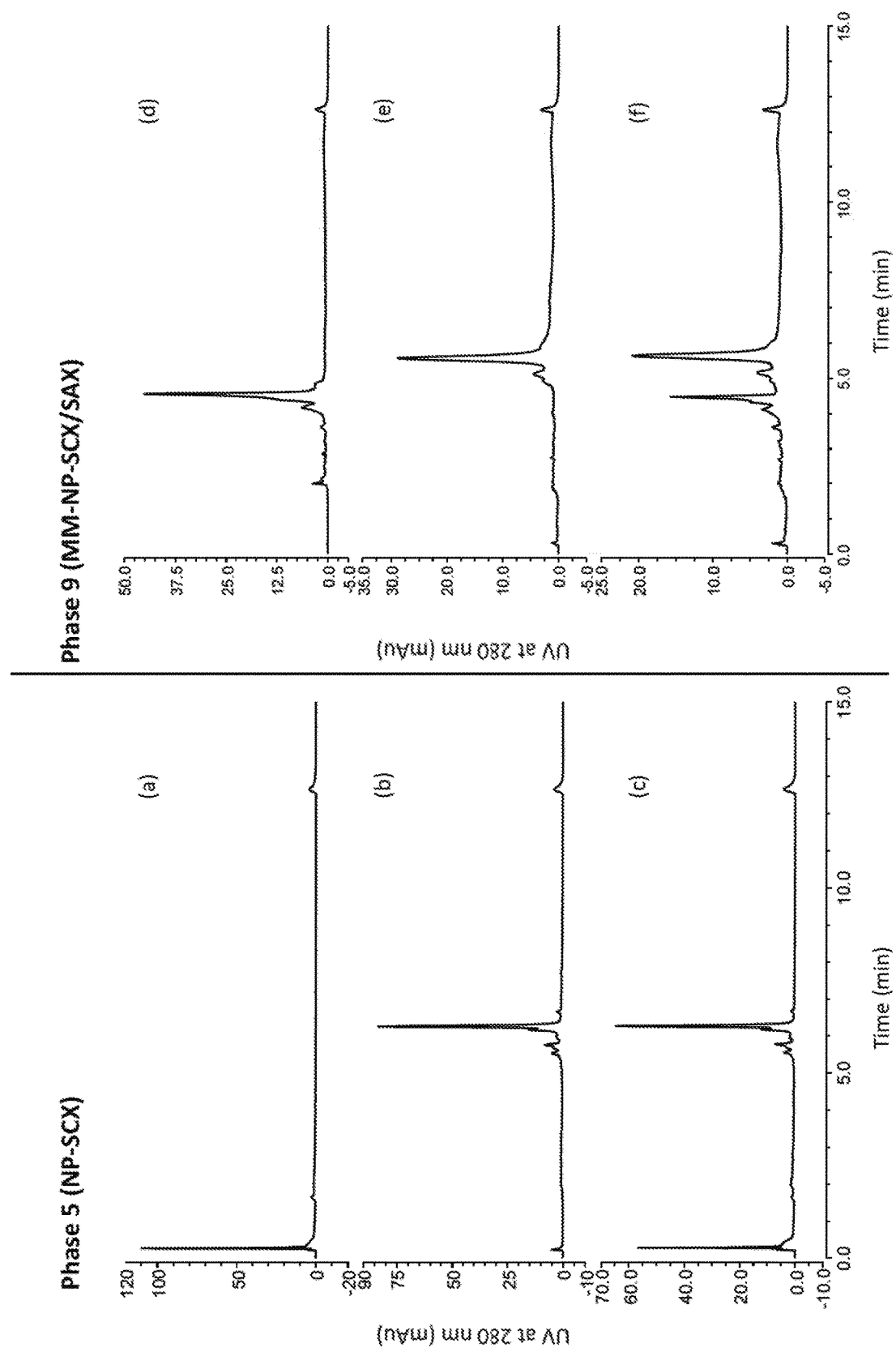
FIG. 4 shows various chromatograms illustrating the simultaneous retention and separation of both low pI and high pI proteins using a chromatographic media (Phase 9 shown in FIG. 2) according to the invention (chromatograms d-f) and using a comparative chromatographic media (Phase 5, chromatograms a-c).

FIG. 4 shows the simultaneous separation of high pI and low pI protein(s) on the multimode (MM) phase (Phase 9) containing cation-exchange (SCX) (on non-porous (NP) particles) with anion-exchange (SAX) nano-size particles. In FIG. 4, chromatograms d-f, the results demonstrate the simultaneous retaining and separation of high pI protein (ribonuclease A, pI 9.6) and low pI protein (trypsin inhibitor, pI 4.55) using a multimode phase (Phase 9) containing a cation-exchange nonporous particle (Phase 5) with anion-exchange nano-size particles (7). FIG. 4, chromatogram a, using Phase 5 alone (cation-exchange media, without opposite charged nano particles), from a run using trypsin inhibitor only, shows that at pH 5.6 trypsin inhibitor (RT at 0.269 min) is not retained on Phase 5 due to electro-static repulsion while chromatogram b from a run using ribonuclease A only shows that ribonuclease A can be retained (RT at 6.257 min) and its charge variants are separated through cation-exchange interactions. FIG. 4, chromatogram c, shows the chromatogram of trypsin inhibitor (RT at 0.286 min) and ribonuclease A (RT at 6.265 min) on Phase 5 with a single injection to reinforce the findings from chromatograms a and b. By comparison, by combining cation-exchange (from Phase 5) and anion-exchange (7) characteristics, Phase 9 can simultaneously retain and separate both low pI proteins (e.g., trypsin inhibitor) and high pI proteins (e.g., ribonuclease A). FIG. 4 chromatograms d, e and f, where d was run with trypsin inhibitor, e was run with ribonuclease A and f was run on a sample of both trypsin and ribonuclease A, show that both proteins were retained and separated.

Example 13

Preparation of WCX(SAX) Multi-Mode Media (Phase 11)
(i) Synthesis of Carboxylated Poly-Divinylbenzene Resin Particles (Phase 10)

A suspension of 10 g Phase 1 in 100 mL D.I. water in a 250 mL round bottom flask was added to 5 g acrylic acid. After purging the resulting mixture with nitrogen for 30 min, 4 g 2,2'-Azobis[2-(2-imidazolin-2-yl)propane]dihydrochloride [CAS NO. 27776-21-2] was introduced to the reaction in series. After stirring at 50° C. for 10 hours, the reaction mixture was filtered off and the cake was washed with 200 mL acetone, 200 mL D.I. water and 200 mL acetone in series to give Phase 10 where n is estimated to range from about 10 to about 30.

(ii) Preparation of WCX(SAX) Multi-Mode Media (Phase 11)

A 4.0×50 mm PEEK LC column was packed with material 10 using a high-pressure slurry packing technique. Separately, 10 mL of an aminated latex solution 7 (of Example 7) was adjusted to pH 7-8 with a phosphate buffer (0.2 M, pH7 to 8). The latex solution was transferred into a 250-mL HPLC eluent bottle. A HPLC pump was used to wash the packed column with a phosphate buffer (0.2 M, pH 7) at 0.5 mL/min for 30 min. The column was then purged with the latex solution at 0.5 mL/min until the latex particles were observed flowing out the exit of the column. Finally, the column was washed with phosphate buffer (0.2 M, pH 7), D.I water, and 70% acetonitrile in D.I. water to afford a column packed with Phase 11.

Example 14

Preparation of SCX(SAX) Multi-Mode Media (Phase 14)

To a slurry of 10 g of 5 μm nonporous spherical polymethacrylate/glycidyl methacrylate/ethyleneglycoldimethacrylate co-polymer resin 12 (surface fully hydroxylated and dried) in 100 mL of dioxane (anhydrous) in a 250-mL round-bottom flask was added 10 g of 1,3-propanesultone. After stirring under reflux for 20 hours, the reaction mixture was filtered off and the cake is washed with 100 mL acetone, 100 mL 250 mM phosphate buffer at pH 7 and 200 mL D.I. water to give Phase 13.

A 4.6×100 mm PEEK LC column was packed with Phase 13 using a high-pressure slurry packing technique. Separately, 10 mL of an aminated latex solution 7 was adjusted to pH 7-8 with a phosphate buffer (0.2 M, pH7 to 8). The latex solution was transferred into a 250-mL HPLC eluent bottle. A HPLC pump was used to wash the packed column with a phosphate buffer (0.2 M, pH 7) at 0.5 mL/min for 30 min. The column was then purged with the latex solution at 0.5 mL/min until the latex particles were observed flowing out the exit of the column. Finally, the column was washed with phosphate buffer (0.2 M, pH 7), D.I water, and 70% acetonitrile in D.I. water to afford a column packed with Phase 14.

The LC columns packed with either Phase 14 or Phase 13, respectively were subjected to the following chromatographic evaluation. The test conditions were as follows: gradient, 20 mM MES and 25 mM NaCl to 20 mM MES and 500 mM NaCl at pH 5.6 over 20 min (where the NaCl concentration increased linearly); flow rate, 1.3 mL/min; injection volume, 5 μL; temperature: 30° C.; detection, UV at 280 nm. The test mixture contained trypsin inhibitor (5 mg/mL) and ribonuclease A (5 mg/mL).

Figure 7:
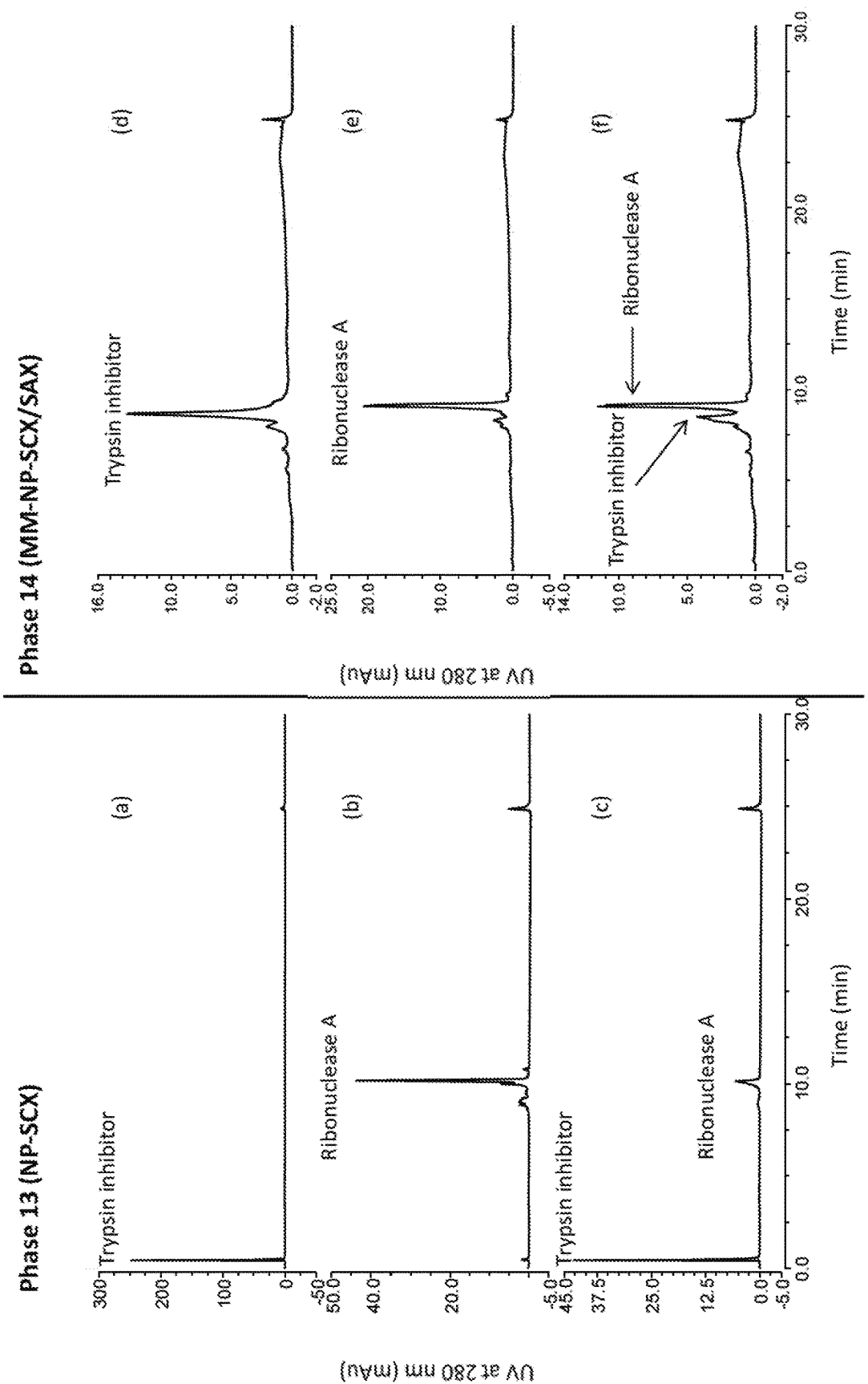
FIG. 7 shows chromatograms illustrating the simultaneous retention and separation of both low pI and high pI proteins using a chromatographic media according to the invention (Phase 14 shown in FIG. 6) in chromatograms d-f and using a comparative chromatographic media (Phase 13) in chromatogram a-c.

FIG. 7 shows the simultaneous separation of high pI and low pI protein(s) on the multimode (MM) phase (Phase 14) containing strong cation-exchange (SCX) (on non-porous (NP) particles) with strong anion-exchange (SAX) nano-size particles. In FIG. 7, chromatograms d-f, the results demonstrate the simultaneous retaining and separation of high pI protein (ribonuclease A, pI 9.6) and low pI protein (trypsin inhibitor, pI 4.55) using a multimode phase (Phase 14) containing a cation-exchange layer on non-porous particle (Phase 13) with anion-exchange nano-size particles (7). FIG. 7, chromatogram a, using Phase 13 alone (cation-exchange media, without opposite charged nano particles), from a run using trypsin inhibitor only, shows that at pH 5.6 trypsin inhibitor is not retained on Phase 13 due to electro-static repulsion. Chromatogram b from a run using ribonuclease A only shows that ribonuclease A can be retained and its charge variants are separated through cation-exchange interactions. FIG. 7, chromatogram c, shows the chromatogram of trypsin inhibitor and ribonuclease A on Phase 13 with a single injection to reinforce the findings from chromatograms a and b. By comparison, by combining cation-exchange (from Phase 13) and anion-exchange (7) characteristics, Phase 14 can simultaneously retain and separate both low pI proteins (e.g., trypsin inhibitor) and high pI proteins (e.g., ribonuclease A). FIG. 7 chromatograms d, e and f, where d was run with trypsin inhibitor, e was run with ribonuclease A and f was run on a sample of both trypsin inhibitor and ribonuclease A, show that both proteins were retained and separated.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising"

and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A chromatographic media for separating bio-polymers, the chromatographic media having cationic and anionic retention modes, the chromatographic media comprising:
   non-porous substrate particles including an organic polymer, the non-porous substrate particles having a neutral hydrophilic layer at an external surface thereof, the neutral hydrophilic layer configured to reduce a binding of the bio-polymers directly to the non-porous substrate particles compared to a binding of the bio-polymers to the non-porous substrate particles without the neutral hydrophilic layer;
   a charged first ion exchange layer bound to the substrate particles on top of the neutral hydrophilic layer, the first ion exchange layer comprising a plurality of polymer chains, each polymer chain of the plurality of polymer chains having a length and being bound to the substrate particles such that each of the polymer chains extends away from the substrate particles in a direction orthogonal to the external surfaces thereof, and each polymer chain comprising between 5 and 100 first ion exchange groups distributed along the length thereof;
   a charged second ion exchange layer comprising charged nano-particles bound to the substrate particles on top of the first ion exchange layer, the second ion exchange layer comprising second ion exchange groups, the second ion exchange layer having an opposite charge to the first ion exchange layer and being bound to the substrate particles by electrostatic interactions with the first ion exchange layer,
   wherein the first ion exchange layer provides one of the cationic and anionic retention modes and the second ion exchange layer provides the other one of the cationic and anionic retention modes,
   wherein the first and second ion exchange layers both reside on the exterior surface of the non-porous substrate particles and are configured such that for each charged nano-particle of the second ion exchange layer, the charged nano-particle partially interpenetrates a respective group of polymer chains of the plurality of polymer chains of the first ion exchange layer and electrostatically interacts with a first portion of the between 5 and 100 of the first ion exchange groups carried by each of the polymer chain of said respective group of polymer chains, and such that a second portion of the between 5 and 100 of the first ion exchange groups carried by each of the polymer chains of the same respective group of polymer chains remain spatially separated from the charged nano-particles, such that in aggregate the charged nano-particles of the second ion exchange layer reduce the retention properties of the first ion exchange layer, as measured by retention time, by less than 50%,
   wherein the respective group of polymer chains of at least some different charged nano-particles are non-overlapping one with another,
   and wherein both the cationic and anionic retention modes are accessible to bind the bio-polymers.

2. The chromatographic media of claim 1, wherein the neutral hydrophilic layer is a fully hydroxylated layer.

3. The chromatographic media of claim 2, wherein the fully hydroxylated layer is provided by surface polymerization, polymer adsorption, cross-linking, or any combination thereof on the surface of the substrate particles.

4. The chromatographic media of claim 3, wherein the fully hydroxylated layer is provided by polymerizing a glycidyl monomer on the surface of the substrate particles.

5. The chromatographic media of claim 4, wherein the glycidyl monomer comprises a triglycidyl ether.

6. The chromatographic media of claim 1, wherein the non-porous substrate particles include a divinylbenzene-based organic polymer.

7. The chromatographic media of claim 6, wherein the non-porous substrate particles include a divinylbenzene polymer or a styrene-divinylbenzene co-polymer.

8. The chromatographic media of claim 1, wherein a retention time of a molecule retained by the first ion exchange layer is not changed by more than 20% by the presence of the second ion exchange layer on top of the first ion exchange layer.

9. The chromatographic media of claim 1, wherein either (i) the first ion exchange groups are cation exchange groups and are selected from negatively charged sulfonate groups and negatively charged carboxylate groups, and the second ion exchange groups are anion exchange groups and are positively charged quaternary amine groups; or (ii) the first ion exchange groups are anion exchange groups and are positively charged quaternary amine groups, and the second ion exchange groups are cation exchange groups and are selected from negatively charged sulfonate groups and negatively charged carboxylate groups.

10. The chromatographic media of claim 1, wherein the nano-particles comprise cross-linked latex particles having a median diameter in the range of 1 to 1000 nm.

11. The chromatographic media of claim 10, wherein the cross-linked latex particles have a degree of crosslinking in the range from 2 to 20%.

12. The chromatographic media of claim 10, wherein the cross-linked latex particles comprise a methacrylate-based polymer.

13. The chromatographic media of claim 1, wherein the median diameter of the substrate particles is in the range 1 to 20 μm.

14. The chromatographic media of claim 1, wherein the surface area of the substrate particles is in the range 0.5 to 10 m²/g.

15. The chromatographic media of claim 1, disposed in a chromatography column or a solid phase extraction column.

16. A method of liquid chromatography comprising separating protein species in a liquid sample by flowing the sample in an eluent through the chromatography column of claim 15.

17. A method of preparing a chromatographic media having cationic and anionic retention modes, the method comprising the steps:
providing non-porous substrate particles including an organic polymer, the non-porous substrate particles having a neutral hydrophilic layer at a surface of the non-porous substrate particles, in which the neutral hydrophilic layer is configured to reduce a binding of bio-polymers directly to the non-porous substrate particles compared to a binding of the bio-polymer to the non-porous substrate particles without the neutral hydrophilic layer;
attaching a first ion exchange layer comprising first ion exchange groups onto the neutral hydrophilic layer on the substrate particles, thereby forming a plurality of polymer chains bound to the substrate particles, each of the polymer chains extends away from the substrate particles in a direction orthogonal to the external surfaces thereof, each polymer chain of the plurality of polymer chains having a length and each polymer chain comprising between 5 and 100 of the first ion exchange groups distributed along the length thereof; and
attaching a second ion exchange layer onto the substrate particles on top of the first ion exchange layer, the second ion exchange layer comprising charged nano-particles comprising second ion exchange groups, the second ion exchange layer having an opposite charge to the first ion exchange layer,
wherein the first and second ion exchange layers both reside on the exterior surface of the non-porous substrate particles and are configured such that for each charged nano-particle of the second ion exchange layer, the charged nano-particle partially interpenetrates a respective group of polymer chains of the plurality of polymer chains of the first ion exchange layer and electrostatically interacts with a first portion of the between 5 and 100 of the first ion exchange groups carried by each of the polymer chains, and such that a second portion of the between 5 and 100 of the first ion exchange groups carried by each of the polymer chains of the same respective group of polymer chains remain spatially separated from the charged nano-particles, such that in aggregate the charged nano-particles of the second ion exchange layer reduce the retention properties of the first ion exchange layer, as measured by retention time, by less than 50%,
wherein the respective group of polymer chains of at least some different charged nano-particles are non-overlapping one with another,
and wherein both the cationic and anionic retention modes are accessible to bind the bio-polymer.

18. The method of preparing a chromatographic media of claim 17, wherein the step of providing the substrate particles having a neutral hydrophilic layer at their surface comprises providing the substrate particles having a fully hydroxylated layer at their surface.

19. The method of preparing a chromatographic media of claim 17, wherein the step of providing the substrate particles having a neutral hydrophilic layer at their surface comprises encapsulating the substrate particles with a fully hydroxylated layer through surface polymerization, polymer adsorption, cross-linking, or any combination thereof.

20. The method of preparing a chromatographic media of claim 19, wherein the step of encapsulating the substrate particles with a fully hydroxylated layer comprises polymerization of a triglycidyl ether on the surface of the substrate particles.

21. The method of preparing a chromatographic media of claim 17, wherein the step of attaching the first ion exchange layer onto the substrate particles comprises one of the steps (i)-(ii):
  i. grafting the first ion exchange layer onto the substrate particles by polymerizing ionic monomers or precursors of ionic monomers; or
  ii. grafting the first ion exchange layer onto the substrate particles by polymerizing epoxide monomers, followed by converting of epoxide groups to anion-exchange or cation-exchange functionality via ring opening reactions.

22. The method of preparing a chromatographic media of claim 17, wherein the second layer is attached in step (c) by contacting a slurry of the substrate particles functionalized with the first ion-exchange layer in a liquid medium with a slurry of charged polymer nano-particles.

23. The method of preparing a chromatographic media of claim 17, wherein the second layer is attached to the substrate particles in step (c) by providing a column packed with the substrate particles functionalized with the first ion-exchange layer as a stationary phase, connecting the column to a pump and pumping a solution or suspension of charged polymer nano-particles through the column such that nano-particles bind to the surface of the substrate particles.

24. A chromatographic media prepared by the method of claim 17.

* * * * *